(12) United States Patent
Cordonnier et al.

(10) Patent No.: US 11,984,205 B2
(45) Date of Patent: *May 14, 2024

(54) NON-FUNGIBLE TOKEN SYSTEMS AND METHODS FOR STORING AND ACCESSING HEALTHCARE DATA

(71) Applicant: Carlsmed, Inc., Carlsbad, CA (US)

(72) Inventors: Michael J. Cordonnier, Carlsbad, CA (US); Shariq Hussain, Vista, CA (US); Niall Patrick Casey, Carlsbad, CA (US)

(73) Assignee: Carlsmed, Inc., Carlsbad, CA (US)

( * ) Notice: Subject to any disclaimer, the term of this patent is extended or adjusted under 35 U.S.C. 154(b) by 73 days.

This patent is subject to a terminal disclaimer.

(21) Appl. No.: 17/878,633

(22) Filed: Aug. 1, 2022

(65) Prior Publication Data
US 2023/0268040 A1 Aug. 24, 2023

Related U.S. Application Data

(63) Continuation of application No. 17/678,874, filed on Feb. 23, 2022, now Pat. No. 11,443,838.

(51) Int. Cl.
G16H 10/65 (2018.01)
G16H 40/20 (2018.01)
(Continued)

(52) U.S. Cl.
CPC .............. *G16H 10/65* (2018.01); *G16H 40/20* (2018.01); *H04L 9/0643* (2013.01);
(Continued)

(58) Field of Classification Search
None
See application file for complete search history.

(56) References Cited

U.S. PATENT DOCUMENTS 4,704,686 A 11/1987 Aldinger
4,936,862 A 6/1990 Walker et al.
(Continued)

FOREIGN PATENT DOCUMENTS

CN 104318009 A 1/2015
CN 104353121 A 2/2015
(Continued)

OTHER PUBLICATIONS

Endo, Kenji et al. "Measurement of whole spine sagittal alignment using the SLOT radiography of the SONIALVISION satire series clinical application." Medical Now, No. 78; Aug. 2015, 4 pages.
(Continued)

*Primary Examiner* — Kristy A Haupt
(74) *Attorney, Agent, or Firm* — Perkins Coie LLP

(57) ABSTRACT

Systems and methods for storing and accessing healthcare data in blockchain managed digital filing cabinets are disclosed. The system can receive and store patient healthcare data from sources such as wearable devices, an implant, patient devices, healthcare provider devices, databases, cloud storage accounts, healthcare databases, or digital filing cabinets. The system can convert the healthcare into non-fungible tokens on a blockchain to protect the healthcare data from being accessed by nefarious actors. The system can manage access to the healthcare data based on authentication rules.

21 Claims, 8 Drawing Sheets

(51) Int. Cl.
*H04L 9/00* (2022.01)
*H04L 9/06* (2006.01)
*H04L 9/08* (2006.01)
*H04W 4/80* (2018.01)

(52) U.S. Cl.
CPC ............. *H04L 9/0816* (2013.01); *H04W 4/80* (2018.02); *H04L 9/50* (2022.05)

(56) References Cited

U.S. PATENT DOCUMENTS

| | | |
|---|---|---|
| 5,431,562 A | 7/1995 | Andreiko et al. |
| D420,995 S | 2/2000 | Imamura |
| D436,580 S | 1/2001 | Navano |
| 6,315,553 B1 | 11/2001 | Sachdeva |
| 6,540,512 B1 | 4/2003 | Sachdeva |
| 6,696,073 B2 | 2/2004 | Boyce et al. |
| 6,772,026 B2 | 8/2004 | Bradbury |
| 6,932,842 B1 | 8/2005 | Litschko et al. |
| 6,978,188 B1 | 12/2005 | Christensen |
| 6,988,241 B1 | 1/2006 | Guttman |
| 7,174,282 B2 | 2/2007 | Hollister et al. |
| 7,187,790 B2 | 3/2007 | Sabol et al. |
| D548,242 S | 8/2007 | Viegers |
| D614,191 S | 4/2010 | Takano |
| 7,747,305 B2 | 6/2010 | Dean et al. |
| 7,756,314 B2 | 7/2010 | Karau et al. |
| 7,799,077 B2 | 9/2010 | Lang |
| D633,514 S | 3/2011 | Tokunaga |
| D656,153 S | 3/2012 | Imamura |
| 8,246,680 B2 | 8/2012 | Betz |
| 8,265,949 B2 | 9/2012 | Haddad |
| 8,275,594 B2 | 9/2012 | Lin |
| 8,337,507 B2 | 12/2012 | Lang |
| 8,394,142 B2 | 3/2013 | Bertagnoli |
| 8,457,930 B2 | 6/2013 | Shroeder |
| 8,532,806 B1 | 9/2013 | Masson |
| 8,556,983 B2 | 10/2013 | Bojarski et al. |
| 8,644,568 B1 | 2/2014 | Hoffman |
| 8,735,773 B2 | 5/2014 | Lang |
| 8,758,357 B2 | 6/2014 | Frey |
| 8,775,133 B2 | 7/2014 | Schroeder |
| 8,781,557 B2 | 7/2014 | Dean |
| 8,843,229 B2 | 9/2014 | Vanasse |
| 8,855,389 B1 | 10/2014 | Hoffman |
| 8,870,889 B2 | 10/2014 | Frey |
| 9,020,788 B2 | 4/2015 | Lang |
| D735,231 S | 7/2015 | Omiya |
| D737,309 S | 8/2015 | Kito |
| 9,198,678 B2 | 12/2015 | Frey et al. |
| 9,208,558 B2 | 12/2015 | Dean |
| D757,025 S | 5/2016 | Kim |
| D761,842 S | 7/2016 | Johnson |
| 9,411,939 B2 | 8/2016 | Furrer |
| 9,445,907 B2 | 9/2016 | Meridew |
| 9,452,050 B2 | 9/2016 | Miles et al. |
| D774,076 S | 12/2016 | Fuller |
| 9,542,525 B2 | 1/2017 | Arisoy et al. |
| 9,642,633 B2 | 5/2017 | Frey et al. |
| 9,693,831 B2 | 7/2017 | Mosnier et al. |
| 9,707,058 B2 | 7/2017 | Bassett |
| 9,715,563 B1 | 7/2017 | Schroeder |
| D797,760 S | 9/2017 | Tsujimura |
| D797,766 S | 9/2017 | Ibsies |
| D798,312 S | 9/2017 | Tsujimura |
| 9,757,245 B2 | 9/2017 | O'Neil et al. |
| D798,894 S | 10/2017 | Ibsies |
| 9,775,680 B2 | 10/2017 | Bojarski et al. |
| 9,782,228 B2 | 10/2017 | Mosnier et al. |
| D812,628 S | 3/2018 | Okado |
| 9,993,341 B2 | 6/2018 | Vanasse |
| 10,034,676 B2 | 7/2018 | Donner |
| D825,605 S | 8/2018 | Jann |
| D826,977 S | 8/2018 | Nakajima |
| 10,089,413 B2 | 10/2018 | Wirx-Speetjens et al. |
| D841,675 S | 2/2019 | Hoffman |
| 10,213,311 B2 | 2/2019 | Mafhouz |
| D845,973 S | 4/2019 | Jaycobs |
| D845,974 S | 4/2019 | Cooperman |
| D847,165 S | 4/2019 | Kolbenheyer |
| D848,468 S | 5/2019 | Ng |
| D849,029 S | 5/2019 | Cooperman |
| D849,773 S | 5/2019 | Jiang |
| 10,292,770 B2 | 5/2019 | Ryan |
| 10,299,863 B2 | 5/2019 | Grbic et al. |
| D854,560 S | 7/2019 | Field |
| D854,561 S | 7/2019 | Field |
| 10,390,958 B2 | 8/2019 | Maclennan |
| D860,237 S | 9/2019 | Li |
| D860,238 S | 9/2019 | Bhardwaj |
| D866,577 S | 11/2019 | Eisert |
| D867,379 S | 11/2019 | Ang |
| D867,389 S | 11/2019 | Jamison |
| 10,463,433 B2 | 11/2019 | Turner et al. |
| D870,762 S | 12/2019 | Mendoza |
| 10,512,546 B2 | 12/2019 | Kamer et al. |
| 10,517,681 B2 | 12/2019 | Roh et al. |
| D872,117 S | 1/2020 | Kobayashi |
| D872,756 S | 1/2020 | Howell |
| D874,490 S | 2/2020 | Dodsworth |
| D875,761 S | 2/2020 | Heffernan |
| D876,454 S | 2/2020 | Knowles |
| D876,462 S | 2/2020 | Li |
| D877,167 S | 3/2020 | Knowles |
| D879,112 S | 3/2020 | Hejazi |
| 10,588,589 B2 | 3/2020 | Bregman-Amitai et al. |
| 10,603,055 B2 | 3/2020 | Donner et al. |
| D880,513 S | 4/2020 | Wang |
| D881,908 S | 4/2020 | Sunil |
| D881,910 S | 4/2020 | Lin |
| 10,621,289 B2 | 4/2020 | Schroeder |
| 10,631,988 B2 | 4/2020 | Arnold et al. |
| D884,008 S | 5/2020 | Thornberg |
| 10,646,236 B2 | 5/2020 | Donner et al. |
| 10,646,258 B2 | 5/2020 | Donner et al. |
| 10,736,698 B2 | 8/2020 | Bohl |
| 10,751,188 B2 | 8/2020 | Guo et al. |
| D896,825 S | 9/2020 | Abel |
| D896,828 S | 9/2020 | Linares |
| D898,054 S | 10/2020 | Everhart |
| D899,438 S | 10/2020 | Crafts |
| 10,806,597 B2 | 10/2020 | Sournac et al. |
| 10,902,944 B1 | 1/2021 | Casey et al. |
| D916,868 S | 4/2021 | Evangeliou |
| D916,879 S | 4/2021 | Mitsumori |
| D918,253 S | 5/2021 | Choe |
| 11,000,334 B1 | 5/2021 | Young |
| D921,675 S | 6/2021 | Kmak |
| D921,677 S | 6/2021 | Kmak |
| D921,687 S | 6/2021 | Kmak |
| D924,909 S | 7/2021 | Nasu |
| D925,567 S | 7/2021 | Hayamizu |
| D927,528 S | 8/2021 | Heisler |
| 11,083,586 B2 | 8/2021 | Cordonnier |
| 11,112,770 B2 | 9/2021 | Roh et al. |
| D933,692 S | 10/2021 | Smith |
| 11,166,764 B2 | 11/2021 | Roh et al. |
| D937,870 S | 12/2021 | Pinto |
| D937,876 S | 12/2021 | Harvey |
| D938,461 S | 12/2021 | Hoffman |
| D938,986 S | 12/2021 | Grossberg |
| D940,178 S | 1/2022 | Ang |
| D946,022 S | 3/2022 | Nuttbrown |
| D946,023 S | 3/2022 | Nuttbrown |
| D946,024 S | 3/2022 | Vogler-Lvashchanka |
| D946,616 S | 3/2022 | Tsai |
| D958,151 S | 7/2022 | Casey et al. |
| 11,376,076 B2 | 7/2022 | Casey et al. |
| 11,432,943 B2 | 9/2022 | Casey et al. |
| 11,439,514 B2 | 9/2022 | Casey et al. |
| 11,443,838 B1 * | 9/2022 | Cordonnier ............ G16H 40/20 |
| 2004/0104512 A1 | 6/2004 | Eidenschink |
| 2005/0273170 A1 | 12/2005 | Navarro et al. |
| 2007/0276501 A1 | 11/2007 | Betz |

(56) References Cited

U.S. PATENT DOCUMENTS

| | | |
|---|---|---|
| 2008/0227047 A1 | 9/2008 | Lowe |
| 2009/0062739 A1 | 3/2009 | Anderson |
| 2010/0324692 A1 | 12/2010 | Uthgenannt |
| 2012/0150243 A9 | 6/2012 | Crawford et al. |
| 2012/0322018 A1 | 12/2012 | Lowe |
| 2013/0323669 A1 | 12/2013 | Lowe |
| 2014/0072608 A1 | 3/2014 | Karagkiozaki |
| 2014/0074438 A1 | 3/2014 | Furrer |
| 2014/0081659 A1 | 3/2014 | Nawana et al. |
| 2014/0086780 A1 | 3/2014 | Miller |
| 2014/0100886 A1 | 4/2014 | Woods |
| 2014/0164022 A1 | 6/2014 | Reed |
| 2014/0263674 A1 | 9/2014 | Cerveny |
| 2014/0350614 A1 | 11/2014 | Frey |
| 2015/0079533 A1 | 3/2015 | Lowe |
| 2015/0089590 A1 | 3/2015 | Krishnan et al. |
| 2015/0105891 A1 | 4/2015 | Golway et al. |
| 2015/0199488 A1 | 7/2015 | Falchuk |
| 2015/0213225 A1 | 7/2015 | Amarasingham |
| 2015/0324490 A1 | 11/2015 | Page |
| 2015/0328004 A1 | 11/2015 | Mafhouz |
| 2015/0332018 A1 | 11/2015 | Rosen |
| 2016/0001039 A1 | 1/2016 | Armour et al. |
| 2016/0015465 A1 | 1/2016 | Steines et al. |
| 2016/0030067 A1 | 2/2016 | Frey et al. |
| 2016/0074048 A1 | 3/2016 | Pavlovskaia |
| 2016/0117817 A1 | 4/2016 | Seel |
| 2016/0143744 A1 | 5/2016 | Bojarski et al. |
| 2016/0184054 A1 | 6/2016 | Lowe |
| 2016/0210374 A1 | 7/2016 | Mosnier et al. |
| 2016/0217268 A1 | 7/2016 | Otto |
| 2016/0242857 A1 | 8/2016 | Scholl |
| 2016/0300026 A1 | 10/2016 | Bogoni et al. |
| 2016/0354039 A1 | 12/2016 | Soto et al. |
| 2016/0378919 A1 | 12/2016 | McNutt et al. |
| 2017/0000566 A1 | 1/2017 | Gordon |
| 2017/0014169 A1 | 1/2017 | Dean |
| 2017/0020679 A1 | 1/2017 | Maclennan |
| 2017/0035514 A1 | 2/2017 | Fox et al. |
| 2017/0061375 A1 | 3/2017 | Laster |
| 2017/0068792 A1 | 3/2017 | Reiner |
| 2017/0135706 A1 | 5/2017 | Frey et al. |
| 2017/0143494 A1 | 5/2017 | Mahfouz |
| 2017/0143831 A1 | 5/2017 | Varanasi et al. |
| 2017/0216047 A1 | 8/2017 | Hawkes et al. |
| 2017/0220740 A1 | 8/2017 | D'Urso |
| 2017/0252107 A1 | 9/2017 | Turner et al. |
| 2017/0262595 A1 | 9/2017 | Vorhis |
| 2017/0340447 A1 | 11/2017 | Mahfouz |
| 2017/0354510 A1 | 12/2017 | O'Neil et al. |
| 2017/0367645 A1 | 12/2017 | Klinder |
| 2018/0008349 A1 | 1/2018 | Gillman |
| 2018/0113992 A1 | 4/2018 | Eltorai et al. |
| 2018/0116727 A1 | 5/2018 | Caldwell et al. |
| 2018/0168499 A1 | 6/2018 | Bergold |
| 2018/0168731 A1 | 6/2018 | Reid |
| 2018/0185075 A1 | 7/2018 | She |
| 2018/0233222 A1 | 8/2018 | Daley |
| 2018/0233225 A1 | 8/2018 | Experton |
| 2018/0250075 A1 | 9/2018 | Cho |
| 2018/0303552 A1 | 10/2018 | Ryan |
| 2018/0303616 A1 | 10/2018 | Bhattacharyya et al. |
| 2018/0308569 A1 | 10/2018 | Luellen |
| 2018/0338841 A1 | 11/2018 | Miller et al. |
| 2019/0065685 A1 | 2/2019 | Pickover |
| 2019/0201106 A1 | 7/2019 | Siemionow |
| 2019/0262084 A1 | 8/2019 | Roh et al. |
| 2019/0266597 A1 | 8/2019 | Mohtar |
| 2019/0328929 A1 | 10/2019 | Kugler et al. |
| 2019/0333622 A1 | 10/2019 | Levin |
| 2019/0354693 A1 | 11/2019 | Yoon |
| 2019/0380792 A1 | 12/2019 | Poltaretskyi et al. |
| 2020/0021570 A1 | 1/2020 | Lin |
| 2020/0078180 A1 | 3/2020 | Casey et al. |
| 2020/0085509 A1 | 3/2020 | Roh et al. |
| 2020/0170802 A1 | 6/2020 | Casey et al. |
| 2020/0258605 A1 | 8/2020 | Blechman |
| 2020/0261156 A1 | 8/2020 | Schmidt |
| 2020/0289288 A1 | 9/2020 | Müller et al. |
| 2020/0315708 A1 | 10/2020 | Mosnier et al. |
| 2020/0351094 A1 | 11/2020 | Canterbury et al. |
| 2021/0059822 A1 | 3/2021 | Casey et al. |
| 2021/0064605 A1* | 3/2021 | Bálint ................... H04W 12/35 |
| 2021/0145519 A1 | 5/2021 | Mosnier et al. |
| 2021/0210189 A1 | 7/2021 | Casey et al. |
| 2021/0287770 A1 | 9/2021 | Anderson |
| 2021/0342909 A1 | 11/2021 | Ketchell, III |
| 2021/0382457 A1 | 12/2021 | Roh et al. |
| 2021/0391040 A1 | 12/2021 | Dormer et al. |
| 2022/0000625 A1 | 1/2022 | Cordonnier |
| 2022/0006642 A1 | 1/2022 | Maj et al. |
| 2022/0039965 A1 | 2/2022 | Casey et al. |
| 2022/0047402 A1 | 2/2022 | Casey et al. |
| 2022/0110686 A1 | 4/2022 | Roh et al. |
| 2022/0160405 A1 | 5/2022 | Casey et al. |
| 2022/0160518 A1 | 5/2022 | Casey et al. |

FOREIGN PATENT DOCUMENTS

| | | |
|---|---|---|
| CN | 204468348 U | 7/2015 |
| CN | 105796214 A | 7/2016 |
| CN | 106202861 | 12/2016 |
| CN | 107220933 | 9/2017 |
| CN | 108670506 A | 10/2018 |
| CN | 110575289 A | 12/2019 |
| CN | 111281613 A | 6/2020 |
| CN | 112155792 A | 1/2021 |
| CN | 113643790 | 11/2021 |
| EP | 3120796 A1 | 1/2017 |
| WO | 9507509 A1 | 3/1995 |
| WO | 2004110309 A2 | 12/2004 |
| WO | 2010151564 A1 | 12/2010 |
| WO | 2012154534 A1 | 11/2012 |
| WO | 2014180972 A2 | 11/2014 |
| WO | 2016172694 A1 | 10/2016 |
| WO | 2019112917 A1 | 6/2019 |
| WO | 2019148154 A1 | 8/2019 |
| WO | 2019241167 | 12/2019 |
| WO | 2022045956 A1 | 3/2022 |
| WO | 2023034405 | 3/2023 |

OTHER PUBLICATIONS

Eshkalak, S.K. et al., "The role of three-dimensional printing in healthcare and medicine." Materials and Design 194, Jul. 10, 2020, 15 pages.

Extended European Search Report for European Application No. 18885367.5, dated Aug. 16, 2021, 8 pages.

Extended European Search Report for European Application No. 19859930.0, dated Jun. 22, 2022, 7 pages.

International Search Report and Written Opinion for International Application No. PCT/US19/50885, dated Jan. 28, 2020, 21 pages.

International Search Report and Written Opinion for International Application No. PCT/US19/63855, dated Feb. 14, 2020, 15 pages.

International Search Report and Written Opinion for International Application No. PCT/US21/44878, dated Nov. 16, 2021, 18 pages.

International Search Report and Written Opinion for International Application No. PCT/US21/45503, dated Jan. 11, 2022, 19 pages.

International Search Report and Written Opinion for International Patent Application No. PCT/US21/60074, dated Mar. 17, 2022, 21 pages.

International Search Report and Written Opinion for International Patent Application No. PCT/US2018/063530, dated Feb. 12, 2019, 16 pages.

International Search Report and Written Opinion for International Patent Application No. PCT/US21/12065, dated Apr. 29, 2021, 19 pages.

International Search Report and Written Opinion for International Patent Application No. PCT/US21/59837, dated Feb. 7, 2022, 19 pages.

(56) References Cited

OTHER PUBLICATIONS

Majdouline et al., "Preoperative assessment and evaluation of instrumentation strategies for the treatment of adolescent idiopathic scoliosis: computer simulation and optimization." Scoliosis 7, 21 (2012), pp. 1-8.
Materialise Mimics, "Efficiently turn scans into accurate virtual 3D models," Retrieved on Nov. 1, 2019 at www. materialize.com/en/medical/software/mimics, 1 page.
Pimenta, Dr. Luiz, "Current Surgical Strategies to Restore Proper Sagittal Alignment," Journal of Spine 2015, vol. 4, Issue 4, 2 pages.
Pruthi, G et al., "Comprehensive review of guidelines to practice prosthodontic and implant procedures during COVID-19 pandemic." Journal of Oral Biology and Craniofacial Research 10, Oct. 17, 2020, 8 pages.
U.S. Appl. No. 17/463,054 for Casey et al., filed Aug. 31, 2021.
ISA: United States Patent and Trademark Office, PCT Application No. PCT/US2022/042188, filed Aug. 31, 2022, International Search Report and Written Opinion dated Dec. 29, 2022, 11 pages.
SA: United States Patent and Trademark Office, PCT Application No. PCT/US23/13653, filed Feb. 22, 2023, International Search Report and Written Opinion mailed Jul. 21, 2023, 9 pages.

\* cited by examiner

Share Imaging

Imaging Study

*Current Stage*

2011-95
Apple User
Hospital Patient ID
1/8/21

Imaging Review

Patient Images

Are you planning to upload an image study for this case?
Yes

If so, what type of image study is included in the upload?
CT, X-Ray

Please use this field to upload the image study (DCM files only).

*FIG. 7*

NON-FUNGIBLE TOKEN SYSTEMS AND METHODS FOR STORING AND ACCESSING HEALTHCARE DATA

CROSS-REFERENCE TO RELATED APPLICATION

The present application is a continuation of U.S. patent application Ser. No. 17/678,874, filed Feb. 23, 2022 (now U.S. Pat. No. 11,443,838), which is incorporated herein by reference in its entirety.

TECHNICAL FIELD

The present disclosure is generally related to storing medical records, and more particularly to systems and methods for storing and accessing healthcare data in blockchain managed digital filing cabinets.

BACKGROUND

Blockchain technology is used to transfer assets using tokens generated as part of a blockchain encryption process. An asset (e.g., an electronic coin, a blockchain-based good, a personal identifier, and so on) is represented by a chain of transactions that transfers ownership from one party to another party. To transfer ownership of an asset on a blockchain, a new transaction is generated and added to a stack of transactions in a block. The new transaction, which includes the public key of the new owner, is digitally signed by the owner with the owner's private key to transfer ownership to the new owner as represented by the new owner's public key. Once the block is full, the block is "capped" with a block header that is a hash digest of all the transaction identifiers within the block. The block header is recorded as the first transaction in the next block in the chain, creating a mathematical hierarchy called a "blockchain." To verify the current owner, the blockchain of transactions can be followed to verify each transaction from the first transaction to the last transaction. The new owner need only have the private key that matches the public key of the transaction that transferred the asset. The blockchain creates a mathematical proof of ownership in an entity represented by a security identity (e.g., a public key), which can be pseudo-anonymous.

The blockchain technology can maintain a distributed ledger of transactions. With a distributed ledger, a ledger of all the transactions for an asset is stored redundantly at multiple nodes (i.e., computers) of a blockchain network. The ledger at each node is stored as a blockchain. In a blockchain, the transactions are stored in the order that the transactions are received by the nodes. Each node in the blockchain network has a complete replica of the entire blockchain. The blockchain system also implements techniques to ensure that each node will store the identical blockchain, even though nodes can receive transactions in different orderings. To verify that the transactions in a ledger stored at a node are correct, the blocks in the blockchain can be accessed from oldest to newest, generating a new hash of the block and comparing the new hash to the hash generated when the block was created. If the hashes are the same, then the transactions in the block are verified. The blockchain system also implements techniques to ensure that it would be infeasible to change a transaction and regenerate the blockchain by employing a computationally expensive technique to generate a nonce that is added to the block when it is created. A blockchain ledger is sometimes referred to as an Unspent Transaction Output ("UXTO") set because it tracks the output of all transactions that have not yet been spent.

Numerous types of data associated with patient treatments and records are available. To locate a patient's medical records and health history, physicians often rely on collecting information from the patient at the time of a healthcare appointment or patient data available via the patient's medical record. However, patient data may not be readily available or up to date, or the patient may be unconscious due to, for example, an accident. For example, it is often difficult to obtain information (e.g., manufacturing information, surgical procedure used, etc.) related to surgical implants. Accordingly, conventional methods for protecting patient medical records may lack necessary security.

BRIEF DESCRIPTION OF THE DRAWINGS

The accompanying drawings illustrate various embodiments of systems, methods, and embodiments of various other aspects of the disclosure. Any person with ordinary skill in the art will appreciate that the illustrated element boundaries (e.g., boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles.

FIG. 7 illustrates an exemplary patient data set that may be used in connection with the methods described herein, according to an embodiment.

DETAILED DESCRIPTION

Figure 1:
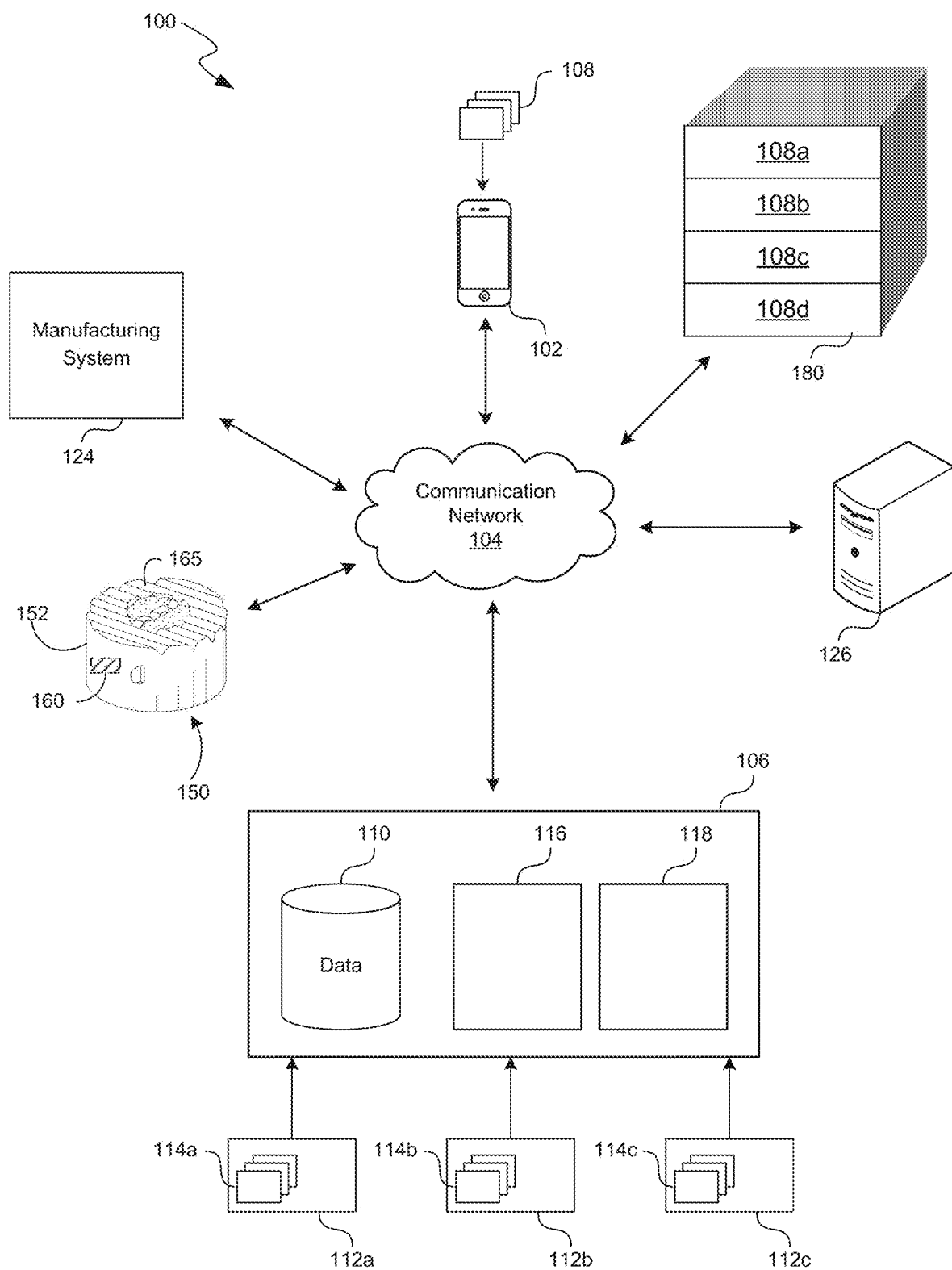
FIG. 1 is a network connection diagram illustrating a system for providing patient-specific medical care, according to an embodiment.

The present technology is directed to systems and methods for storing, managing, and accessing healthcare data in a distributed ledger (e.g., public ledger) and/or blockchain managed digital filing cabinets. For example, in many embodiments, the present technology is directed to providing healthcare data from an implant, such as a patient-specific implant. The system can receive and store patient healthcare data from a source (e.g., wearable device, user device, blockchain device, implant, healthcare provider device, etc.). The system can convert the patient healthcare data into a non-fungible token. The system can manage access to the healthcare data based on authentication levels. The authentication levels can include, without limitation, authenticating a user based on geolocation, biometric data, blockchain, tokens (e.g., non-fungible tokens), or any authentication method. Based on the determined authentication level of the user requesting access to the healthcare data on the implant, the system can permit the user to access some or all of the healthcare data. The system can include one or more healthcare digital filing cabinets that store healthcare data, patient information, electronic medical records, and/or additional patient related information. In some embodiments, systems can share data (e.g., healthcare data, patient information, electronic medical records, and/or additional patient related information) via a network without using digital filing cabinets.

The healthcare data can be managed using one or more digital filing cabinets. A user can approve family members, physicians, healthcare providers, or other users to access selected data, types of data, data associated with the procedure, data associated with the user, or the like. The digital filing cabinet can contain, for example, surgical plans, implant data, health records, medical insurance information, digital wallets, and other healthcare data. In some implementations, the digital filing cabinet can automatically update the healthcare data based on received data. In some implementations, the digital filing cabinet can automatically receive data from user devices, such as wearable devices, smartphones, non-fungible tokens (NFTs), or other devices capable of collecting biometrics of the user. The user's digital filing cabinet can link one or more accounts to provide communication between the accounts. For example, the accounts can be healthcare provider accounts, family member accounts, insurance provider accounts, government entity accounts, or other accounts that allow the digital filing cabinet to request and receive data. The user can manage third-party access (e.g., viewing only, editing, annotation, etc.) of the stored data within an NFT (e.g., containerized NFTs), NFT-linked data (e.g., data linked to NFTs), etc. This allows the user to authorize, for example, a physician access to view data collected in real-time or almost real-time. The physician can provide real-time or almost real-time feedback to the patient via the digital filing cabinet. The patient can use the digital filing cabinet or a patient account to, for example, review physician feedback, a diagnosis, a treatment plan (e.g., a surgical plan, interventional plan, therapy plan, etc.), predicted treatment outcomes, cost estimates, insurance information, or the like.

The data management system can lock digital filing cabinets in response to failed authorization attempts, notify users of potential fraudsters, fraudulent activity, etc. The data management system can analyze collected data to generate post-treatment plans. In some embodiments, the data managing system can use one or more models to analyze post-operative collected data to generate or modify post-treatment plans, such as therapy plans, new surgical plans, etc. Post-operative analytics can be stored in digital filing cabinets or other databases. This allows the data management system to periodically or continuously analyze data from different data sources to provide patient-specific healthcare. The data management system can select a model (e.g., machine learning model) selected based on the available data. If new data comes available, the data management system can identify one or more models suitable for analyzing the newly available data. This allows the data management system to adaptively select machine learning models to enhance analytics. The data sources can include, without limitation, diagnostic equipment (e.g., imaging equipment), patient wearables, hospital diagnostic equipment, etc.

In some embodiments, a healthcare management system includes digital filing cabinets that integrate data from, for example, digital wallets, one or more devices associated with the user, or data sources associated with a physician/healthcare provider. The healthcare management system can generate post-operative analytics based on post-operative data, such as new scans of the patient, diagnostic data, new patient medical records, or the like can be used. The healthcare management system can manage authentication, patient wallets, and/or digital filing cabinets via, for example, automated settings, privacy management, updated record management, etc.

In some embodiments, point of care devices can be integrated with a healthcare management system. Data from the point of care devices can be automatically transmitted to the patient's digital filing cabinet. This allows patients to access the digital filing cabinets (e.g., implant manufacture managed digital filing cabinets, healthcare provider managed digital filing cabinets, etc.) and view and/or manage data in real-time or almost real-time.

In some embodiments, the healthcare management system can use blockchain with NFT techniques to store and authenticate access to the healthcare data. The healthcare management system can use blockchain technology to convert healthcare data (e.g., patient information, surgery details, imaging studies, EMRs, implant information, and/or additional patient related information) into NFTs. The healthcare management system can create a digital key for each user (e.g., patient, healthcare provider, insurance provider, family member, etc.) and rules (e.g., smart contract) regarding authorization to access the healthcare data. Converting healthcare data to an NFT(s) can protect the user's healthcare data from being accessed by nefarious actors or unauthorized users. For example, the since the NFT(s) is digitally stored on the blockchain, the NFT(s) is immutable (e.g., can't be changed) and distributed (e.g., output is validated by the blockchain network), making it difficult for a nefarious actor to access the healthcare data. The NFT can include metadata containing the healthcare data that is stored on-chain or off-chain. In some embodiments, containerized NFTs can store data on the blockchain. The healthcare data can be converted into a containerized NFT containing the healthcare data on a distributed ledger. In some implementations, healthcare NFTs store large files, such as imaging data, scans, etc. on the distributed ledger. The large files can be tokenized (e.g., compressed, converted, etc.) into a healthcare NFT or distributed between multiple healthcare NFTs. The configuration of the healthcare NFT can be selected to store, for example, metadata, healthcare data, containerized data, surgical procedure data, medical device data, or other data disclosed herein.

In some embodiments, the healthcare data can be linked to NFT(s). For example, at least a portion of the healthcare data and the linked NFT can be stored on different blockchains. In some implementations, a first portion of the healthcare data can be stored as containerized data as part of a first NFT on a first blockchain. A second NFT can be linked to a second portion of the healthcare data stored on a second blockchain. In some embodiments, the healthcare data can be stored on decentralized storage systems, centralized storage systems, etc. For example, a non-fungible token platform can automatically link stored patient's healthcare data to a newly created NFT that includes one or more links to metadata, healthcare data, or other data disclosed herein. The non-fungible token platform ("NFT platform") can determine the location of NFT-linked data based on, for example, one or more of file size, authentication levels, encryption, hash protocols, smart contracts, or the like. For example, large file size NFT-linked healthcare data (e.g., high-resolution imaging, scans, etc.) can be stored in decentralized or centralized digital filing cabinets managed by, for example, a healthcare provider, hospital, etc. Small file size NFT-linked healthcare data can be stored in the blockchain or ledger. In some implementations, a user can select the stored location of data associated with the NFT and can use decentralized storage (e.g., interplanetary file systems), peer-to-peer hypermedia protocols, NFT platforms or marketplaces, or other systems to store NFTs and NFT-related data. A healthcare data NFT platform can include multiple NFT platforms each configured to create and manage NFT(s) according to different protocols.

Without being bound by theory, using a healthcare data management platform to perform various aspects of the surgical plans described herein is expected to provide several advantages over conventional operative techniques. For example, storing, analyzing, managing, and accessing healthcare data in digital filing cabinets may improve data security of patient information, decrease patient recovery time by giving them access to health metrics and areas to improve, decrease patient stress for pre-procedures and post procedures by having access to medical information (e.g., x-ray images, procedure routines, etc.), shorten analysis/assessment time of patients because healthcare providers can access the patients information in real-time or almost real-time from the patient's implant, and alert the patient and healthcare providers of implant updates or recalls from the implant manufacturer.

In representative embodiments, the foregoing method can be performed by a system storing computer-executable instructions that, when executed, cause the system to perform the steps of the method.

In some embodiments, a computer-implemented method includes linking to a patient-managed account storing patient data associated with a patient-specific implant. The method includes receiving patient data from a patient-managed account. The received patient data is analyzed to identify a relevant training parameter. A reference data set is generated based on the relevant training parameter. The machine learning models are trained based at least in part on the reference data set for designing implants similar to the patient-specific implant. In some embodiments, the relevant training parameter can be a categorized spinal condition, wherein the categorization is based on one or more predetermined thresholds. The predetermined thresholds can include a threshold level-specific lumbar lordosis, a threshold Cobb angle, a threshold pelvic incidence, and/or a threshold disc height. In some embodiments, the received patient data includes at least one of comparing the received patient data to pre-operative data of the patient or identifying at least a portion of the patient data for the reference data set based on the comparison. Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

The words "comprising," "having," "containing," and "including," and other forms thereof, are intended to be equivalent in meaning and be open-ended in that an item or items following any one of these words is not meant to be an exhaustive listing of such item or items, or meant to be limited to only the listed item or items.

As used herein and in the appended claims, the singular forms "a," "an," and "the" include plural references unless the context clearly dictates otherwise.

Although the disclosure herein primarily describes systems and methods for storing and accessing healthcare data in a digital filing cabinet associated with an implant, plan (e.g., surgical plan, treatment plan, etc.), the technology may be applied equally to medical treatment and devices in other fields (e.g., other types of medical practices) with or without utilizing digital filing cabinets. Additionally, although many embodiments herein describe systems and methods with respect to implanted devices, the technology may be applied equally to other types of medical technologies and devices (e.g., non-implanted devices).

FIG. 1 is a network connection diagram illustrating a computing system 100 for storing and accessing healthcare data in digital filing cabinets, according to an embodiment. As described in further detail herein, the system 100 is configured to collect, store, monitor, and/or update healthcare data. System 100 can include one or more digital filing cabinets 180 that can contain, without limitation, one or more electronic health records (EHRs), EMRs, patient information, digital wallets (e.g., signed messages, keys, cryptocurrency, tokens, credit cards, payment information, etc.), and other healthcare data. The digital filing cabinet 180 can receive and convert the healthcare data into a digital format to increase the efficiency of locating and retrieving healthcare data.

The computing system 100 can function as a cryptographic platform. The digital filing cabinet 180 can use blockchain technology to convert the healthcare data to cryptographic tokens. In some embodiments, the computing system 100 is configured to operate as an NFT platform based on blockchain technology. Using blockchain technology can increase the security of the healthcare data based on the authentication requirements of users to access the data. NFTs can provide verification of digital healthcare data by authenticating access credentials (e.g., public and private keys), eliminating tampering of data (data integrity), and providing a source of truth for a patient's health record. NFTs can provide ownership of data, accessibility to data, portability of data, patient-specific solutions based on the verifiable patient data, patient-specific algorithms for treatment(s), patient-selectable sharing of data, trackable usages of patient data, and generate economic value for use of data. Using blockchain technology and NFTs can provide system 100 with a method to securely track, identify ownership, link to, and/or transfer the healthcare data (e.g., transfer to intended recipients). In some embodiments, the NFTs can have an expiration date to access the data, confirmation of intended recipient, instructions for implantation (e.g., surgical robot), traceable chain of custody (e.g., supply chain), ensure authenticity (elimination of counterfeit products) of the data, and payment (reimbursement) for product (verified, traceable) in cryptocurrency.

The digital filing cabinet 180 can receive the healthcare data from a patient, healthcare provider(s), medical insurance entities, banking entities, and/or storage devices with healthcare data. Based on the type of healthcare data, the digital filing cabinet 180 can organize the healthcare data by authentication levels. For example, the patient can access all the healthcare data, but the healthcare provider is limited to medical records and cannot access the patient's medical insurance or payment information. The digital filing cabinet 180 contains the patient healthcare data 108 and organizes the patient healthcare data by different authentication levels, such as data 108a, 108b, 108c, and 108d. Each group or set of healthcare data 108a, 108b, 108c, and 108d requires a different level of authentication for a user to access. Example healthcare datasets and healthcare data are discussed in connection with FIGS. 7-8. Once the authentication level of a user is identified, the system 100 can send the healthcare data associated with the identified authentication level to the user. In some implementations, the system 100 sends the healthcare data to the patient's implant 150 for the user to retrieve or to a user device.

The number of groups of healthcare data, permission settings, stored data, organizational schemes, and/or other configurations can be set by the user, healthcare provider, or the like. Data can be automatically collected and incorporated into the appropriate group of data. In cloud-based implementations, the digital filing cabinet 180 can be stored on a cloud server to provide remote access. In some implementations, the digital filing cabinet 180 can be stored locally to provide access to records at any time. Additionally, local storage of the digital filing cabinets 180 with digital wallets containing blockchain information can be stored locally. Each group of healthcare data 108a, 108b, 108c, and 108d can be associated by the user (or data management system) with, for example, a procedure, a physician, a healthcare provider, and/or medical manufacture. The user can add information, including annotation, personal notes, and other information that may or may not be viewable by other users, to the healthcare data 108a, 108b, 108c and 108d and can select the type, amount, and/or level of authorization/access. In some implementations, the healthcare data 108a, 108b, 108c and 108d can include blockchain data, wallets, NFT(s), NFT-linked data, containerized data, keys, unique IDs, encryption programs, etc.

In some embodiments, a group of healthcare data 108a can be associated with an implant 150 in the patient (not shown) and can include a surgical plan for the implant 150, manufacturing data for the implant 150, notifications (e.g., recall notifications), predicted post-treatment analytics, physician information, and other information (e.g., pre-operative, intra-operative, and/or post-operative information) associated with the implant 150 or procedure. The user can set one or more rules for allowing authorized user(s) to access (e.g., all or a portion of) the healthcare data 108a or healthcare data 108. For example, the user can authorize viewing of post-operative data 108a by a physical therapist who can access post-operative collected data to modify therapy plans for the user. The user can authorize a primary care physician access to the healthcare data 108 to provide general healthcare treatment and can authorize a surgeon access to the healthcare data 108a to evaluate surgical outcomes and recommend additional treatments, such as future surgical interventions.

The healthcare data 108b can include, for example, general electronic medical records (EMRs) of the patient, including health records not associated with the implant. The user can authorize a primary care physician access to the healthcare data 108b to provide general healthcare treatment. The user can authorize family members and third parties access to the healthcare data 108b. Accordingly, the access settings for the healthcare data 108a and 108b can be the same or different.

The healthcare data 108c can include, for example, data from a user device input. The data can be from, for example, wearables (e.g., smartwatches, pedometers, etc.), smartphones, biometric sensors (e.g., analyte sensors, glucose sensors, etc.), heart monitors, exercise monitoring equipment, or the like. The user can authorize family members to access the data 108c to help with compliance with, for example, dietary goals, exercise goals, or other user goals.

Data can be automatically provided to the digital filing cabinet 180. In some embodiments, for example, an implant retrieval feature 160 can provide instructions for accessing the digital filing cabinet 180. An imaging apparatus (e.g., an MRI machine, x-ray machine, scanner, etc.) can read information from the retrieval feature 160. The information included can be transmitted, via communication network 104, to the digital filing cabinet 180. The transmitted information can include, without limitation, authorization information (e.g., digital filing cabinet login information), patient identification, implant identifier, and/or other information to use to authorize, locate, and/or categorize data.

The digital filing cabinet 180 can store data transmitted, via the communication network 104, from manufacturing system 124 and can analyze received data and correlate the data, such as manufacturing data, with the received implant data. Correlation settings can be modified or set by the user. Additionally, surgical plans can be transmitted, via the communication network 104, from the system 106 to the digital filing cabinet 180. The surgical plan can be associated with the manufacturing data, implant data, and other information associated with the implant 150. The digital filing cabinet 180 can send, via the communication network 104, patient healthcare data to the system 106. This allows newly available data to be automatically or periodically transmitted to the analysis system 106. The analysis system 106 can analyze the newly received data using, for example, one or more models to provide analytics to the client computing device 102, digital filing cabinet 180, manufacturing system 124, physician, etc. The client computing device 102 can receive analytics and notifications from, for example, the digital filing cabinet 180, analysis system 106, and/or other data sources.

In some embodiments, the system 100 is configured to manage patient healthcare data on user devices, cloud-based devices, and/or healthcare provider devices. The healthcare data can include patient medical records, medical insurance information, health metrics from wearable devices, surgical information, surgical plans, technology recommendations (e.g., device and/or instrument recommendations), and/or medical device information (e.g., an implanted medical device (also referred to herein as an "implant" or "implanted device") or implant delivery instrument). The digital wallet can be used to manage blockchain healthcare data (e.g., blockchain EHRs, EMRs, etc.), insurance actions (e.g., payments, claim submissions, etc.), or the like.

In some embodiments, the system 100 manages the authentication required to access the medical records. The authentication can include blockchain, tokens, keys, biometrics, geolocation, passwords, or any authentication credentials. Healthcare data that is particular to a patient, is referred to herein as a "patient-specific" or "personalized" healthcare data. The digital filing cabinet 180 can store one or more keys (e.g., private keys, public keys, etc.), authentication information, and/or other information for accessing data, including electronic medical records associated with a patient from a distributed blockchain ledger of electronic medical records. U.S. application Ser. No. 17/463,054 discloses systems and methods for tracking patient medical records using, for example, keys and is incorporated by reference in its entirety. The system 100 can include systems and features for linking medical devices with patient data as disclosed in U.S. patent Ser. No. 16/990,810, which is incorporated by reference in its entirety. Digital filing cabinets can be used to receive user feedback as described in U.S. application Ser. No. 16/699,447, which is incorporated by reference in its entirety. The system disclosed herein can include digital filing cabinets for designing medical devices using the methods disclosed in U.S. application Ser. No. 16/699,447.

The system 100 includes a client computing device 102, which can be a user device, such as a smartphone, mobile device, laptop, desktop, personal computer, tablet, phablet, wearable device (e.g., smartwatch), or other such devices known in the art. As discussed further herein, the client computing device 102 can include one or more processors, and memory storing instructions executable by the one or more processors to perform the methods described herein. The client computing device 102 can be associated with a healthcare provider or a patient. Although FIG. 1 illustrates a single client computing device 102, in alternative embodiments, the client computing device 102 can instead be implemented as a client computing system encompassing a plurality of computing devices, such that the operations described herein with respect to the client computing device 102 can instead be performed by the computing system and/or the plurality of computing devices.

The client computing device 102 is configured to receive patient healthcare data 108 associated with a patient. The patient healthcare data 108 can include data representative of the patient's condition, anatomy, pathology, medical history, preferences, and/or any other information or parameters relevant to the patient. For example, the patient healthcare data 108 can include medical history, surgical intervention data, treatment outcome data, progress data (e.g., physician notes), patient feedback (e.g., feedback acquired using quality of life questionnaires, surveys), clinical data, provider information (e.g., physician, hospital, surgical team), patient information (e.g., demographics, sex, age, height, weight, type of pathology, occupation, activity level, tissue information, health rating, comorbidities, health related quality of life (HRQL)), vital signs, diagnostic results, medication information, allergies, image data (e.g., camera images, Magnetic Resonance Imaging (MRI) images, ultrasound images, Computerized Aided Tomography (CAT) scan images, Positron Emission Tomography (PET) images, X-Ray images), diagnostic equipment information (e.g., manufacturer, model number, specifications, user-selected settings/configurations, etc.), or the like. In some embodiments, the patient healthcare data 108 includes data representing one or more of patient identification number (ID), age, gender, body mass index (BMI), lumbar lordosis, Cobb angle(s), pelvic incidence, disc height, segment flexibility, bone quality, rotational displacement, range of motion, disability score, and/or treatment level of the spine. In some embodiments, the client computing device 102 can locally store the digital filing cabinet 180, healthcare data 108, and/or other information. The client computing device 102 can store account information for allowing the user to automatically access remote digital filing cabinets or accounts with or without login credentials. In some embodiments, the client computing device 102 can periodically or continuously receive newly available data (e.g., biometrics from wearables, user input, etc.) and can transmit all of or a portion of the newly available data to, for example, remote storage systems, such as the digital filing cabinet 180, server 106, or the like.

The client computing device 102 is operably connected via a communication network 104 to a server 106, thus allowing for data transfer between the client computing device 102 and the server 106. The communication network 104 may be a wired and/or a wireless network. The communication network 104, if wireless, may be implemented using communication techniques such as Visible Light Communication (VLC), Worldwide Interoperability for Microwave Access (WiMAX), Long term evolution (LTE), Wireless local area network (WLAN), Infrared (IR) communication, Public Switched Telephone Network (PSTN), Radio waves, and/or other communication techniques known in the art.

The server 106, which may also be referred to as a "healthcare data network" or "healthcare data analytics network," can include one or more computing devices and/or systems. As discussed further herein, the server 106 can include one or more processors, and memory storing instructions executable by the one or more processors to perform the methods described herein. In some embodiments, the server 106 is implemented as a distributed "cloud" computing system or facility across any suitable combination of hardware and/or virtual computing resources.

The cloud analytics integration platform 126 is connected to the communication network 104. The analytics integration platform 126 can analyze the healthcare data and integrate data collected from the patient and healthcare providers into the digital filing cabinet. The analytics integration platform 126 can integrate surgical plans and patient plan, identify health metrics of concern for the patient, display patient information and goals, perform post-operative analytics, and generate healthcare provider or patient notifications (e.g., monitoring based on data from wearables, requesting updated information, scheduling appointments, or notifying of emergencies).

The medical implant 150 can be an intervertebral device that includes a body 152 configured to interface with one or more identified anatomical structures (e.g., one or more vertebral bodies or endplates) at and/or proximate the target implantation site (e.g., between one or more vertebral bodies or endplates). The implant body 152 can include one or more structural features designed to engage one or more identified anatomical structures. For example, in the illustrated embodiment, the implant 150 can include an upper surface 165 and a lower surface (not shown) configured to seat against vertebral bodies of the spine. In some embodiments, the upper surface 165 and the lower surface can have contours that match contours of the vertebral endplates, such that the upper surface 165 and lower surface "mate" with the corresponding vertebral endplates they engage with. The dimensions, contours, topology, composition, and/or other implant data can be part of the EMR. In some embodiments, such as the illustrated embodiment, the upper surface 165 and/or the lower surface can be textured (e.g., via roughenings, knurlings, ridges, and the like). Texturing data can be part of the manufacturing data stored in the EMRs. For lordotic correction, the upper surface 165 and the lower surface may be angled with respect to one another, and the EMR can include the angle and sizes of these surfaces.

A user (e.g., a physician, healthcare provider, patient, etc.) can access EMRs using a retrieval feature 160. For example, in embodiments in which the retrieval feature 160 is a barcode corresponding to the unique identifier, the user can scan the retrieval feature 160 using, for example, one or more cameras on the computing device and/or otherwise input the unique identifier into the computing device. Once the unique identifier is inputted into the computing system, the computing system can send the unique identifier to a remote server (e.g., via a communication network) with a request to provide the corresponding patient-specific healthcare data set. In response to the request, and as described above, the server can locate the specific data set associated with the unique identifier and transmit the data set to the computing device for display to the user. The implant 150 can include other features assisting with accessing the ledger and viewing the EMRs.

The retrieval feature 160 can be used to carry patient data, such as one or more NFTs, keys (e.g., private keys for unlocking patient medical records stored on a blockchain ledger), or blockchain data. The medical implant 150 can be blockchain-enabled to establish communicative contact using a proximity communication mode. A private key stored on the retrieval feature 160 can be used to access the patient-specific healthcare data. In some implementations, the medical implant 150 also contains a private blockchain ledger for tracking EMRs associated with the patient. As the patient undergoes various treatments, new EMRs and updates to existing EMRs for the patient are generated and stored as "transactions" in a blockchain ledger. To access the EMRs associated with the patient, the private key from the medical implant 150 must be used to "unlock" the EMRs stored in the blockchain ledger. The patient can provide this private key to healthcare providers and other interested parties by a secure platform, mobile application, digital key, or the like. In some embodiments, the EMRs are encrypted using an encryption key that the healthcare provider decrypts. Additionally or alternatively, re-keying protocols, certification management protocols (e.g., enrollment certification protocol, transaction certification protocol, etc.), and other protocols can be utilized for variable access and permissions. The patient can manage the data of the EMR to share selected data only. For example, the patient can keep a section of the EMR private while sharing another section of the EMR. The system also allows for user-controlled settings, such as settings for minors, family members, relatives, and/or other user-controlled settings.

An EMR can include patient data associated with the implant design and design process. If the implant is an artificial disc, for example, the stored data can include kinematic data (e.g., pre-operative patient data, target kinematic data, etc.), manufacturing data, design parameters, target service life data, physician recommendations/notes, etc. The disc can include an articulating implant body with plates contoured to match vertebral endplates, custom articulating members between the plates for providing patient-specific motion, etc. If the implant is an intervertebral cage, the stored data can include materials specifications of the implant body, dimensions of the implant body, manufacturing data, design parameters, target service life data, physician recommendations/notes, etc. The applications and patents incorporated by reference disclose data (e.g., surgical plans, implant specifications, data sets, etc.) that can be associated with the retrieval feature 160.

In some implementations, the patient can set variable permissions for access to transactions and details stored in the blockchain ledger. For example, particular medical providers may only be given access to certain transactions related to particular kinds of medical procedures. In other implementations, permissions can be set based on the patient, such as having child settings for children with an implant.

The medical implant 150 can also track and monitor various health related data for the patient. For example, the medical implant 150 can include one or more sensors configured to measure pressures, loads, or forces applied by anatomical elements to monitor, for example, activity, loading, etc. The medical implant 150 can continuously or periodically collect data indicating activity level, activities performed, disease progression, or the like. For example, loading across the implant 150 can be tracked over a period of time. The applications and patents incorporated by reference disclose techniques for monitoring, collecting data, and transmitting data. In some embodiments, the medical implant 150 can identify events, such as excess loading, imbalance of the spine, or the like. In some embodiments, the patient is monitored with automatic blockchain updating based on activity (e.g., surgical procedure, change in status, etc.), disability (e.g., new disability, progression of disability, etc.), and/or healthcare events. The healthcare events can include imaging, diagnosis, treatment, and/or outcomes and event data that can be encoded in the blockchain. Collected data can be used as historical patient data used to treat another patient. The applications and patents incorporated by reference also disclose usage of historical data, imaging data, surgical plans, simulations, modeled outcomes, treatment protocols, and outcome values that can be encoded in the blockchain. The digital filing cabinets can also track and monitor various health related data for the patient and can include one or more digital wallets, such as blockchain digital wallets for managing blockchain data, ledger wallets, etc. The number, configuration, and/or contents of digital wallets can be selected by the user, physician, etc. The digital wallets can be used to access blockchains to automatically update blockchains for any number of implants.

In some implementations, two or more implants can be used. For example, a patient can have both a spinal implant with an encoded chip containing the private key and/or the private blockchain ledger containing the EMRs of the patient and a subcutaneous digital implant. The subcutaneous digital implant acts as an intermediary device, communicating with both the spinal implant containing the private key and/or the private blockchain ledger and an external computing device, such as a patient treatment computing system. The subcutaneous digital implant may also include data of its own, such as patient identifying information, biometric data, and the like. In some embodiments, the subcutaneous digital implant may include the private key and/or the private blockchain ledger containing the EMRs of the patient. The patient-specific implant can be any of the implants described herein or in any patent references incorporated by reference herein. For example, the patient-specific implant can include one or more of screws (e.g., bone screws, spinal screws, pedicle screws, facet screws), interbody implant devices (e.g., intervertebral implants), cages, plates, rods, discs, fusion devices, spacers, rods, expandable devices, stents, brackets, ties, scaffolds, fixation devices, anchors, nuts, bolts, rivets, connectors, tethers, fasteners, joint replacements (e.g., artificial discs), hip implants, or the like. A patient-specific implant design can include data representing one or more of physical properties (e.g., size, shape, volume, material, mass, weight), mechanical properties (e.g., stiffness, strength, modulus, hardness), and/or biological properties (e.g., osteointegration, cellular adhesion, anti-bacterial properties, anti-viral properties) of the implant. For example, a design for an orthopedic implant can include implant shape, size, material, and/or effective stiffness (e.g., lattice density, number of struts, location of struts, etc.).

Additional implant types, configurations, and structural features suitable for engaging identified anatomical features are described, for example, in U.S. application Ser. No. 16/207,116, filed Dec. 1, 2018, and U.S. application Ser. No. 16/987,113, filed Aug. 6, 2020, the disclosures of which are incorporated by reference herein in their entireties. For example, the medical implants can be pedicle screws, patient-specific implants, interbody implant systems, artificial discs, expandable intervertebral implants, sacroiliac implants, plates, arthroplasty devices for orthopedic joints, non-structural implants, or other devices disclosed in the patents and applications incorporated herein by reference.

The medical implant 150 can be used to track and monitor medical data associated with the patient. U.S. Application No. 63/218,190 discloses implants capable of collecting data, assigning weighting/values, and communicating with other devices. The monitoring can be used with prescriptive systems, such as the systems disclosed in U.S. Pat. No. 10,902,944 and U.S. application Ser. No. 17/342,439, which are incorporated by reference in their entireties. For example, the patient's data can be incorporated into one or more training sets for a machine learning system or other systems disclosed in the incorporated by reference patents and applications. The medical implant 150 can also be a multipurpose implant, providing structure to address a medical issue in the body of the patient while also carrying information regarding the patient. For example, the medical implant 150 can be a pacemaker, a plate or pin to correctly position a previously broken bone or set of bones, and the like. NFTs can be used to store, track, authenticate, transmit, and/or handle data disclosed in U.S. Pat. No. 10,902,944 and U.S. application Ser. No. 17/342,439. For example, surgical plans, pre-operative data, post-operative data, outcome analysis, implant designs, transactions, healthcare data, etc. can be managed using NFTs. The digital filing cabinet 180 can also be incorporated into the systems disclosed in U.S. Pat. No. 10,902,944 and U.S. application Ser. No. 17/342,439 to track and monitor patient-managed medical data.

The client computing device 102 and server 106 can individually or collectively perform the various methods described herein for storing and retrieving healthcare data. For example, some or all of the steps of the methods described herein can be performed by the client computing device 102 alone, the server 106 alone, or a combination of the client computing device 102 and the server 106. In some embodiments, the client computing device 102 includes one or more digital filing cabinets 180. Thus, although certain operations are described herein with respect to the server 106, it shall be appreciated that these operations can also be performed by the client computing device 102, and vice-versa.

The server 106 includes at least one database 110 configured to store reference data useful for the providing, managing, or analyzing patient-specific healthcare data from implant methods described herein. The reference data can include historical and/or clinical data from the same or other patients, data collected from prior surgeries and/or other treatments of patients by the same or other healthcare providers, data relating to medical device designs, data collected from study groups or research groups, data from practice databases, data from academic institutions, data from implant manufacturers or other medical device manufacturers, data from imaging studies, data from simulations, clinical trials, demographic data, treatment data, outcome data, mortality rates, or the like.

In some embodiments, the database 110 includes a plurality of reference patient data sets, each patient reference data set associated with a corresponding reference patient. For example, the reference patient can be a patient that previously received treatment or is currently receiving treatment. Each reference patient data set can include data representative of the corresponding reference patient's condition, anatomy, pathology, medical history, disease progression, preferences, and/or any other information or parameters relevant to the reference patient, such as any of the data described herein with respect to the healthcare data 108. In some embodiments, the reference patient data set includes pre-operative data, intra-operative data, and/or post-operative data. For example, a reference patient data set can include data representing one or more of patient ID, age, gender, BMI, lumbar lordosis, Cobb angle(s), pelvic incidence, disc height, segment flexibility, bone quality, rotational displacement, and/or treatment level of the spine. As another example, a reference patient data set can include treatment data regarding at least one treatment procedure performed on the reference patient, such as descriptions of surgical procedures or interventions (e.g., surgical approaches, bony resections, surgical maneuvers, corrective maneuvers, placement of implants or other devices). In some embodiments, the treatment data includes medical device design data for at least one medical device used to treat the reference patient, such as physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties). In yet another example, a reference patient data set can include outcome data representing an outcome of the treatment of the reference patient, such as corrected anatomical metrics, presence of fusion, HRQL, activity level, return to work, complications, recovery times, efficacy, mortality, and/or follow-up surgeries.

In some embodiments, the server 106 receives at least some of the reference patient data sets from a plurality of healthcare provider computing systems (e.g., systems 112a-112c, collectively 112), digital filing cabinets, or combinations thereof. The server 106 can be connected to the healthcare provider computing systems 112 via one or more communication networks (not shown). Each healthcare provider computing system 112 can be associated with a corresponding healthcare provider (e.g., physician, surgeon, medical clinic, hospital, healthcare network, etc.). Each healthcare provider computing system 112 can include at least one reference patient data set (e.g., reference patient data sets 114a-114c, collectively 114) associated with reference patients treated by the corresponding healthcare provider. The reference patient data sets 114 can include, for example, electronic medical records, electronic health records, biomedical data sets, etc. The reference patient data sets 114 can be received by the server 106 from the healthcare provider computing systems 112 and can be reformatted into different formats for storage in the database 110. Optionally, the reference patient data sets 114 can be processed (e.g., cleaned) to ensure that the represented patient parameters are likely to be useful in the treatment planning methods described herein.

As described in further detail herein, the server 106 can be configured with one or more algorithms that generate patient-specific treatment plan data (e.g., treatment procedures, medical devices) based on the reference data. In some embodiments, the patient-specific data is generated based on correlations between the patient data set 108 and the reference data. Optionally, the server 106 can predict outcomes, including recovery times, efficacy based on clinical end points, likelihood of success, predicted mortality, predicted related follow-up surgeries, or the like. In some embodiments, the server 106 can continuously or periodically analyze patient data (including patient data obtained during the patient stay) to determine near real-time or real-time risk scores, mortality prediction, etc.

In some embodiments, the server 106 includes one or more modules for performing one or more steps of the patient-specific treatment planning methods described herein. For example, in the depicted embodiment, the server 106 includes a data analysis module 116 and a treatment planning module 118. In alternative embodiments, one or more of these modules may be combined with each other, or may be omitted. Thus, although certain operations are described herein with respect to a particular module or modules, this is not intended to be limiting, and such operations can be performed by a different module or modules in alternative embodiments.

The data analysis module 116 is configured with one or more algorithms for identifying a subset of reference data from the database 110 that is likely to be useful in developing a patient-specific treatment plan. The database 110 can retrieve or receive data from the client computing device 102, digital filing cabinet 180, or other data source. For example, the data analysis module 116 can compare patient-specific data (e.g., the patient data set 108 received from the client computing device 102) to the reference data from the database 110 (e.g., the reference patient data sets) to identify similar data (e.g., one or more similar patient data sets in the reference patient data sets). The reference data can be updated in real-time or almost real-time using other patient data accessible via the network 104. The comparison can be based on one or more parameters, such as age, gender, BMI, lumbar lordosis, pelvic incidence, and/or treatment levels. The parameter(s) can be used to calculate a similarity score for each reference patient. The similarity score can represent a statistical correlation between the patient data set 108 and the reference patient data set. Accordingly, similar patients can be identified based on whether the similarity score is above, below, or at a specified threshold value. For example, as described in greater detail below, the comparison can be performed by assigning values to each parameter and determining the aggregate difference between the subject patient and each reference patient. Reference patients whose aggregate difference is below a threshold can be considered to be similar patients.

The data analysis module 116 can further be configured with one or more algorithms to select a subset of the reference patient data sets, e.g., based on similarity to the patient data set 108 and/or treatment outcome of the corresponding reference patient. For example, the data analysis module 116 can identify one or more similar patient data sets in the reference patient data sets, and then select a subset of the similar patient data sets based on whether the similar patient data set includes data indicative of a favorable or desired treatment outcome. The outcome data can include data representing one or more outcome parameters, such as corrected anatomical metrics, presence of fusion, HRQL, activity level, complications, recovery times, efficacy, mortality, or follow-up surgeries. As described in further detail below, in some embodiments, the data analysis module 116 calculates an outcome score by assigning values to each outcome parameter. A patient can be considered to have a favorable outcome if the outcome score is above, below, or at a specified threshold value.

In some embodiments, the data analysis module 116 selects a subset of the reference patient data sets based at least in part on user input (e.g., from a clinician, surgeon, physician, or healthcare provider). For example, the user input can be used in identifying similar patient data sets. In some embodiments, weighting of similarity and/or outcome parameters can be selected by a healthcare provider or physician to adjust the similarity and/or outcome score based on clinician input. In further embodiments, the healthcare provider or physician can select the set of similarity and/or outcome parameters (or define new similarity and/or outcome parameters) used to generate the similarity and/or outcome score, respectively.

In some embodiments, the data analysis module 116 includes one or more algorithms used to select a set or subset of the reference patient data sets based on criteria other than patient parameters. For example, one or more algorithms can be used to select the subset based on healthcare provider parameters (e.g., based on healthcare provider ranking/scores such as hospital/physician expertise, number of procedures performed, hospital ranking, etc.) and/or healthcare resource parameters (e.g., diagnostic equipment, facilities, surgical equipment such as surgical robots), or other non-patient related information that can be used to predict outcomes and risk profiles for procedures for the present healthcare provider. For example, reference patient data sets with images captured from similar diagnostic equipment can be aggregated to reduce or limit irregularities due to variation between diagnostic equipment. Additionally, patient-specific treatment plans can be developed for a particular healthcare provider using data from similar healthcare providers (e.g., healthcare providers with traditionally similar outcomes, physician expertise, surgical teams, etc.). In some embodiments, reference healthcare provider data sets, hospital data sets, physician data sets, surgical team data sets, post-treatment data set, and other data sets can be utilized. By way of example, a patient-specific treatment plan to perform a battlefield surgery can be based on reference patient data from similar battlefield surgeries and/or datasets associated with battlefield surgeries. In another example, the patient-specific treatment plan can be generated based on available robotic surgical systems. The reference patient data sets can be selected based on patients that have been operated on using comparable robotic surgical systems under similar conditions (e.g., size and capabilities of surgical teams, hospital resources, etc.).

The treatment planning module 118 is configured with one or more algorithms to generate at least one treatment plan (e.g., pre-operative plans, surgical plans, post-operative plans etc.) based on the output from the data analysis module 116. In some embodiments, the treatment planning module 118 is configured to develop and/or implement at least one predictive model for generating the patient-specific treatment plan, also known as a "prescriptive model." The predictive model(s) can be developed using clinical knowledge, statistics, machine learning, AI, neural networks, or the like. In some embodiments, the output from the data analysis module 116 is analyzed (e.g., using statistics, machine learning, neural networks, AI) to identify correlations between data sets, patient parameters, healthcare provider parameters, healthcare resource parameters, treatment procedures, medical device designs, and/or treatment outcomes. These correlations can be used to develop at least one predictive model that predicts the likelihood that a treatment plan will produce a favorable outcome for the particular patient. The predictive model(s) can be validated, e.g., by inputting data into the model(s) and comparing the output of the model to the expected output.

In some embodiments, the treatment planning module 118 is configured to generate the treatment plan based on previous treatment data from reference patients. For example, the treatment planning module 118 can receive a selected subset of reference patient data sets and/or similar patient data sets from the data analysis module 116, and determine or identify treatment data from the selected subset. The treatment data can include, for example, treatment procedure data (e.g., surgical procedure or intervention data) and/or medical device design data (e.g., implant design data) that are associated with favorable or desired treatment outcomes for the corresponding patient. The treatment planning module 118 can analyze the treatment procedure data and/or medical device design data to determine an optimal treatment protocol for the patient to be treated. For example, the treatment procedures and/or medical device designs can be assigned values and aggregated to produce a treatment score. The patient-specific treatment plan can be determined by selecting treatment plan(s) based on the score (e.g., higher or highest score; lower or lowest score; score that is above, below, or at a specified threshold value). The personalized patient-specific treatment plan can be based on, at least in part, the patient-specific technologies or patient-specific selected technology.

Alternatively or in combination, the treatment planning module 118 can generate the treatment plan based on correlations between data sets. For example, the treatment planning module 118 can correlate treatment procedure data and/or medical device design data from similar patients with favorable outcomes (e.g., as identified by the data analysis module 116). Correlation analysis can include transforming correlation coefficient values to values or scores. The values/scores can be aggregated, filtered, or otherwise analyzed to determine one or more statistical significances. These correlations can be used to determine treatment procedure(s) and/or medical device design(s) that are optimal or likely to produce a favorable outcome for the patient to be treated.

Alternatively or in combination, the treatment planning module 118 can generate the treatment plan using one or more AI techniques. AI techniques can be used to develop computing systems capable of simulating aspects of human intelligence, e.g., learning, reasoning, planning, problem-solving, decision making, etc. AI techniques can include, but are not limited to, case-based reasoning, rule-based systems, artificial neural networks, decision trees, support vector machines, regression analysis, Bayesian networks (e.g., naïve Bayes classifiers), genetic algorithms, cellular automata, fuzzy logic systems, multi-agent systems, swarm intelligence, data mining, machine learning (e.g., supervised learning, unsupervised learning, reinforcement learning), and hybrid systems.

In some embodiments, the treatment planning module 118 generates the treatment plan using one or more trained machine learning models. Various types of machine learning models, algorithms, and techniques are suitable for use with the present technology. In some embodiments, the machine learning model is initially trained on a training data set, which is a set of examples used to fit the parameters (e.g., weights of connections between "neurons" in artificial neural networks) of the model. For example, the training data set can include any of the reference data stored in database 110, such as a plurality of reference patient data sets or a selected subset thereof (e.g., a plurality of similar patient data sets).

In some embodiments, the machine learning model (e.g., a neural network or a naïve Bayes classifier) may be trained on the training data set using a supervised learning method (e.g., gradient descent or stochastic gradient descent). The training dataset can include pairs of generated "input vectors" with the associated corresponding "answer vector" (commonly denoted as the target). The current model is run with the training data set and produces a result, which is then compared with the target, for each input vector in the training data set. Based on the result of the comparison and the specific learning algorithm being used, the parameters of the model are adjusted. The model fitting can include both variable selection and parameter estimation. The fitted model can be used to predict the responses for the observations in a second data set called the validation data set. The validation data set can provide an unbiased evaluation of a model fit on the training data set while tuning the model parameters. Validation data sets can be used for regularization by early stopping, e.g., by stopping training when the error on the validation data set increases, as this may be a sign of overfitting to the training data set. In some embodiments, the error of the validation data set error can fluctuate during training, such that ad-hoc rules may be used to decide when overfitting has truly begun. Finally, a test data set can be used to provide an unbiased evaluation of a final model fit on the training data set.

To generate a treatment plan, the patient data set 108 can be input into the trained machine learning model(s). Additional data, such as the selected subset of reference patient data sets and/or similar patient data sets, and/or treatment data from the selected subset, can also be input into the trained machine learning model(s). The trained machine learning model(s) can then calculate whether various candidate treatment procedures and/or medical device designs are likely to produce a favorable outcome for the patient. Based on these calculations, the trained machine learning model(s) can select at least one treatment plan for the patient. In embodiments where multiple trained machine learning models are used, the models can be run sequentially or concurrently to compare outcomes and can be periodically updated using training data sets. The treatment planning module 118 can use one or more of the machine learning models based the model's predicted accuracy score.

The patient-specific treatment plan generated by the treatment planning module 118 can include at least one patient-specific treatment procedure (e.g., a surgical procedure or intervention) and/or at least one patient-specific medical device (e.g., an implant or implant delivery instrument). A patient-specific treatment plan can include an entire surgical procedure or portions thereof. Additionally, one or more patient-specific medical devices can be specifically selected or designed for the corresponding surgical procedure, thus allowing for the various components of the patient-specific technology to be used in combination to treat the patient.

In some embodiments, the patient-specific treatment procedure includes an orthopedic surgery procedure, such as spinal surgery, hip surgery, knee surgery, jaw surgery, hand surgery, shoulder surgery, elbow surgery, total joint reconstruction (arthroplasty), skull reconstruction, foot surgery, or ankle surgery. Spinal surgery can include spinal fusion surgery, such as posterior lumbar interbody fusion (PLIF), anterior lumbar interbody fusion (ALIF), transverse or transforaminal lumbar interbody fusion (TLIF), lateral lumbar interbody fusion (LLIF), direct lateral lumbar interbody fusion (DLIF), or extreme lateral lumbar interbody fusion (XLIF). In some embodiments, the patient-specific treatment procedure includes descriptions of and/or instructions for performing one or more aspects of a patient-specific surgical procedure. For example, the patient-specific surgical procedure can include one or more of a surgical approach, a corrective maneuver, a bony resection, or implant placement.

In some embodiments, the patient-specific medical device design includes a design for an orthopedic implant and/or a design for an instrument for delivering an orthopedic implant. Examples of such implants include, but are not limited to, screws (e.g., bone screws, spinal screws, pedicle screws, facet screws), interbody implant devices (e.g., intervertebral implants), cages, plates, disks, fusion devices, spacers, rods, expandable devices, stents, brackets, ties, scaffolds, fixation device, anchors, nuts, bolts, rivets, connectors, tethers, fasteners, joint replacements, hip implants, or the like. Examples of instruments include, but are not limited to, screw guides, cannulas, ports, catheters, insertion tools, or the like.

A patient-specific medical device design can include data representing one or more of physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties) of a corresponding medical device. For example, a design for an orthopedic implant can include implant shape, size, material, and/or effective stiffness (e.g., lattice density, number of struts, location of struts, etc.). In some embodiments, the generated patient-specific medical device design is a design for an entire device. Alternatively, the generated design can be for one or more components of a device, rather than the entire device.

In some embodiments, the design is for one or more patient-specific device components that can be used with standard, off-the-shelf components. For example, in a spinal surgery, a pedicle screw kit can include both standard components and patient-specific customized components. In some embodiments, the generated design is for a patient-specific medical device that can be used with a standard, off-the-shelf delivery instrument. For example, the implants (e.g., screws, screw holders, rods) can be designed and manufactured for the patient, while the instruments for delivering the implants can be standard instruments. This approach allows the components that are implanted to be designed and manufactured based on the patient's anatomy and/or surgeon's preferences to enhance treatment. The patient-specific devices described herein are expected to improve delivery into the patient's body, placement at the treatment site, and/or interaction with the patient's anatomy.

In embodiments where the patient-specific treatment plan includes a surgical procedure to implant a medical device, the treatment planning module 118 can also store various types of implant surgery information, such as implant parameters (e.g., types, dimensions), availability of implants, aspects of a pre-operative plan (e.g., initial implant configuration, detection, and measurement of the patient's anatomy, etc.), FDA requirements for implants (e.g., specific implant parameters and/or characteristics for compliance with FDA regulations), or the like. In some embodiments, the treatment planning module 118 can convert the implant surgery information into formats usable for machine-learning based models and algorithms. For example, the implant surgery information can be tagged with particular identifiers for formulas or can be converted into numerical representations suitable for supplying to the trained machine learning model(s). The treatment planning module 118 can also store information regarding the patient's anatomy, such as two- or three-dimensional images or models of the anatomy, and/or information regarding the biology, geometry, and/or mechanical properties of the anatomy. The anatomy information can be used to inform implant design and/or placement.

The treatment plan(s) generated by the treatment planning module 118 can be transmitted via the communication network 104 to the digital filing cabinet 180 and/or client computing device 102 for output to a user (e.g., clinician, surgeon, healthcare provider, patient). In some embodiments, the client computing device 102 includes or is operably coupled to a display for outputting the treatment plan(s). The display can include a graphical user interface (GUI) for visually depicting various aspects of the treatment plan(s). For example, the display can show various aspects of a surgical procedure to be performed on the patient, such as the surgical approach, treatment levels, corrective maneuvers, tissue resection, and/or implant placement. To facilitate visualization, a virtual model of the surgical procedure can be displayed. As another example, the display can show a design for a medical device to be implanted in the patient, such as a two- or three-dimensional model of the device design. The display can also show patient information, such as two- or three-dimensional images or models of the patient's anatomy where the surgical procedure is to be performed and/or where the device is to be implanted. The client computing device 102 can further include one or more user input devices (not shown) allowing the user to modify, select, approve, and/or reject the displayed treatment plan(s).

In some embodiments, the medical device design(s) generated by the treatment planning module 118 can be transmitted from the client computing device 102 and/or server 106 to a manufacturing system 124 for manufacturing an implant or a corresponding medical device. The manufacturing system 124 can be located on-site or off-site. The implant may be manufactured by any suitable manufacturing system (e.g., the manufacturing system 124 shown in FIG. 1). The digital filing cabinet 180 can store the generated medical device design(s), manufacturing data (e.g., CAM data, print data, etc.), manufacturing information, data for generating surgical plans, surgical plans, surgical plan reports, post-operative data (e.g., therapy plans, predicted outcomes, etc.), and/or other information associated with the medical device.

Various types of manufacturing systems are suitable for use in accordance with the embodiments herein. For example, the manufacturing system 124 can be configured for additive manufacturing, such as three-dimensional (3D) printing, stereolithography (SLA), digital light processing (DLP), fused deposition modeling (FDM), selective laser sintering (SLS), selective laser melting (SLM), selective heat sintering (SHM), electronic beam melting (EBM), laminated object manufacturing (LOM), powder bed printing (PP), thermoplastic printing, direct material deposition (DMD), inkjet photo resin printing, or like technologies, or combination thereof. Alternatively or in combination, the manufacturing system 124 can be configured for subtractive (traditional) manufacturing, such as CNC machining, electrical discharge machining (EDM), grinding, laser cutting, water jet machining, manual machining (e.g., milling, lathe/turning), or like technologies, or combinations thereof. The manufacturing system 124 can manufacture one or more patient-specific medical devices based on fabrication instructions or data (e.g., CAD data, 3D data, digital blueprints, stereolithography data, or other data suitable for the various manufacturing technologies described herein). Different components of the system 100 can generate at least a portion of the manufacturing data used by the manufacturing system 124. The manufacturing data can include, without limitation, fabrication instructions (e.g., programs executable by additive manufacturing equipment, subtractive manufacturing equipment, etc.), 3D data, CAD data (e.g., CAD files), CAM data (e.g., CAM files), path data (e.g., print head paths, tool paths, etc.), material data, tolerance data, surface finish data (e.g., surface roughness data), regulatory data (e.g., FDA requirements, reimbursement data, etc.), or the like. The manufacturing system 124 can analyze the manufacturability of the implant design based on the received manufacturing data. The implant design can be finalized by altering geometries, surfaces, etc. and then generating manufacturing instructions. In some embodiments, the server 106 generates at least a portion of the manufacturing data, which is transmitted to the manufacturing system 124. The manufacturing system 124 can receive and send data using, for example, NFTs, ledgers, or the like.

The manufacturing system 124 can generate CAM data, print data (e.g., powder bed print data, thermoplastic print data, photo resin data, etc.), or the like and can include additive manufacturing equipment, subtractive manufacturing equipment, thermal processing equipment, or the like. The additive manufacturing equipment can be 3D printers, stereolithography devices, digital light processing devices, fused deposition modeling devices, selective laser sintering devices, selective laser melting devices, electronic beam melting devices, laminated object manufacturing devices, powder bed printers, thermoplastic printers, direct material deposition devices, or inkjet photo resin printers, or like technologies. The subtractive manufacturing equipment can be CNC machines, electrical discharge machines, grinders, laser cutters, water jet machines, manual machines (e.g., milling machines, lathes, etc.), or like technologies. Both additive and subtractive techniques can be used to produce implants with complex geometries, surface finishes, material properties, etc. The generated fabrication instructions can be configured to cause the manufacturing system 124 to manufacture the patient-specific orthopedic implant that matches or is therapeutically the same as the patient-specific design. The generated fabrication instructions can be tokenized into a fabrication NFT. In some embodiments, the patient-specific medical device can include features, materials, and designs shared across designs to simplify manufacturing. For example, deployable patient-specific medical devices for different patients can have similar internal deployment mechanisms but have different deployed configurations. In some embodiments, the components of the patient-specific medical devices are selected from a set of available prefabricated components and the selected pre-fabricated components can be modified based on the fabrication instructions or data.

Following the treatment of the patient in accordance with the treatment plan, treatment progress can be monitored over one or more time periods to update the data analysis module 116 and/or treatment planning module 118. Post-treatment data can be added to the reference data stored in the database 110 and used for post-operative analytics. The post-treatment data can be used to train machine learning models for developing patient-specific treatment plans, patient-specific medical devices, or combinations thereof.

It shall be appreciated that the components of the system 100 can be configured in many different ways. For example, in alternative embodiments, the database 110, the data analysis module 116 and/or the treatment planning module 118 can be components of the client computing device 102, rather than the server 106. As another example, the database 110, the data analysis module 116, and/or the treatment planning module 118 can be located across a plurality of different servers, computing systems, or other types of cloud-computing resources, rather than at a single server 106 or client computing device 102.

Additionally, in some embodiments, the system 100 can be operational with numerous other computing system environments or configurations. Examples of computing systems, environments, and/or configurations that may be suitable for use with the technology include, but are not limited to, personal computers, server computers, handheld or laptop devices, cellular telephones, wearable electronics, tablet devices, multiprocessor systems, microprocessor-based systems, programmable consumer electronics, network PCs, minicomputers, mainframe computers, distributed computing environments that include any of the above systems or devices, or the like.

Figure 2:
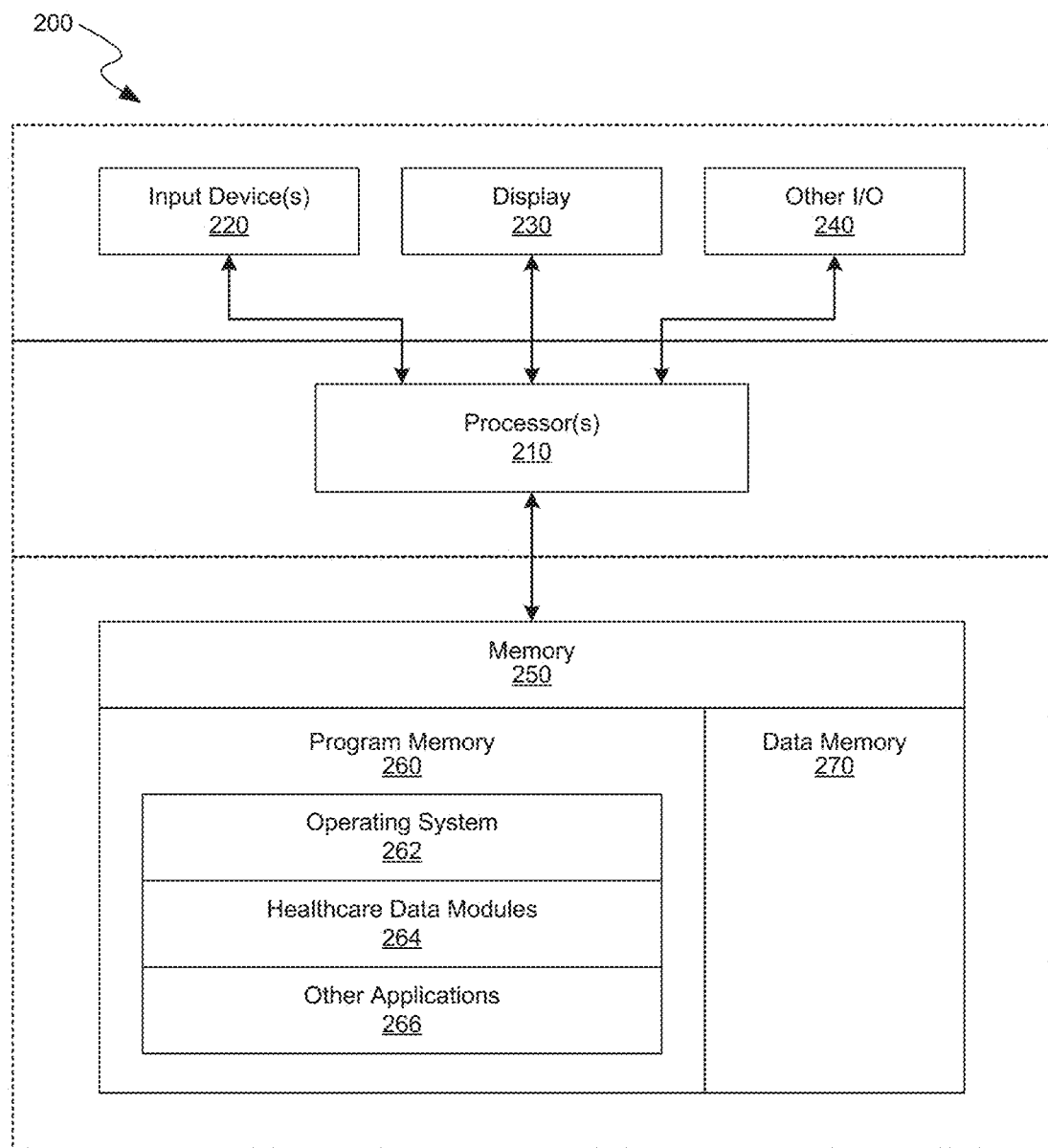
FIG. 2 illustrates a computing device suitable for use in connection with the system of FIG. 1, according to an embodiment.

FIG. 2 illustrates a computing device 200 suitable for use in connection with the system 100 of FIG. 1, according to an embodiment. The computing device 200 can be incorporated in various components of the system 100 of FIG. 1, such as the client computing device 102 or the server 106. The computing device 200 includes one or more processors 210 (e.g., CPU(s), GPU(s), HPU(s), etc.). The processor(s) 210 can be a single processing unit or multiple processing units in a device or distributed across multiple devices. The processor(s) 210 can be coupled to other hardware devices, for example, with the use of a bus, such as a PCI bus or SCSI bus. The processor(s) 210 can be configured to execute one more computer-readable program instructions, such as program instructions to carry out any of the methods described herein.

The computing device 200 can include one or more input devices 220 that provide input to the processor(s) 210, e.g., to notify it of actions from a user of the device 200. The actions can be mediated by a hardware controller that interprets the signals received from the input device and communicates the information to the processor(s) 210 using a communication protocol. Input device(s) 220 can include, for example, a mouse, a keyboard, a touchscreen, an infrared sensor, a touchpad, a wearable input device, a camera- or image-based input device, a microphone, or other user input devices.

The computing device 200 can include a display 230 used to display various types of output, such as text, models, virtual procedures, surgical plans, implants, graphics, and/or images (e.g., images with voxels indicating radiodensity units or Hounsfield units representing the density of the tissue at a location). In some embodiments, the display 230 provides graphical and textual visual feedback to a user. The processor(s) 210 can communicate with the display 230 via a hardware controller for devices. In some embodiments, the display 230 includes the input device(s) 220 as part of the display 230, such as when the input device(s) 220 include a touchscreen or is equipped with an eye direction monitoring system. In alternative embodiments, the display 230 is separate from the input device(s) 220. Examples of display devices include an LCD display screen, an LED display screen, a projected, holographic, or augmented reality display (e.g., a heads-up display device or a head-mounted device), and so on.

Optionally, other I/O devices 240 can also be coupled to the processor(s) 210, such as a network card, video card, audio card, USB, firewire or other external device, camera, printer, speakers, CD-ROM drive, DVD drive, disk drive, or Blu-Ray device. Other I/O devices 240 can also include input ports for information from directly connected medical equipment such as imaging apparatuses, including MRI machines, X-Ray machines, CT machines, etc. Other I/O devices 240 can further include input ports for receiving data from these types of machines from other sources, such as across a network or from previously captured data, for example, stored in a database.

In some embodiments, the computing device 200 also includes a communication device (not shown) capable of communicating wirelessly or wire-based with a network node. The communication device can communicate with another device or a server through a network using, for example, TCP/IP protocols. The computing device 200 can utilize the communication device to distribute operations across multiple network devices, including imaging equipment, manufacturing equipment, etc.

The computing device 200 can include memory 250, which can be in a single device or distributed across multiple devices. Memory 250 includes one or more of various hardware devices for volatile and non-volatile storage, and can include both read-only and writable memory. For example, a memory can comprise random access memory (RAM), various caches, CPU registers, read-only (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory. In some embodiments, the memory 250 is a non-transitory computer-readable storage medium that stores, for example, programs, software, data, or the like. In some embodiments, memory 250 can include program memory 260 that stores programs and software, such as an operating system 262, one or more healthcare data modules 264, and other application programs 266. The healthcare data module(s) 264 can include one or more modules configured to perform the various methods described herein (e.g., the data analysis module 116 and/or treatment planning module 118 described with respect to FIG. 1). Memory 250 can also include data memory 270 that can include, e.g., reference data, configuration data, settings, user options or preferences, etc., which can be provided to the program memory 260 or any other element of the computing device 200.

Figure 3:
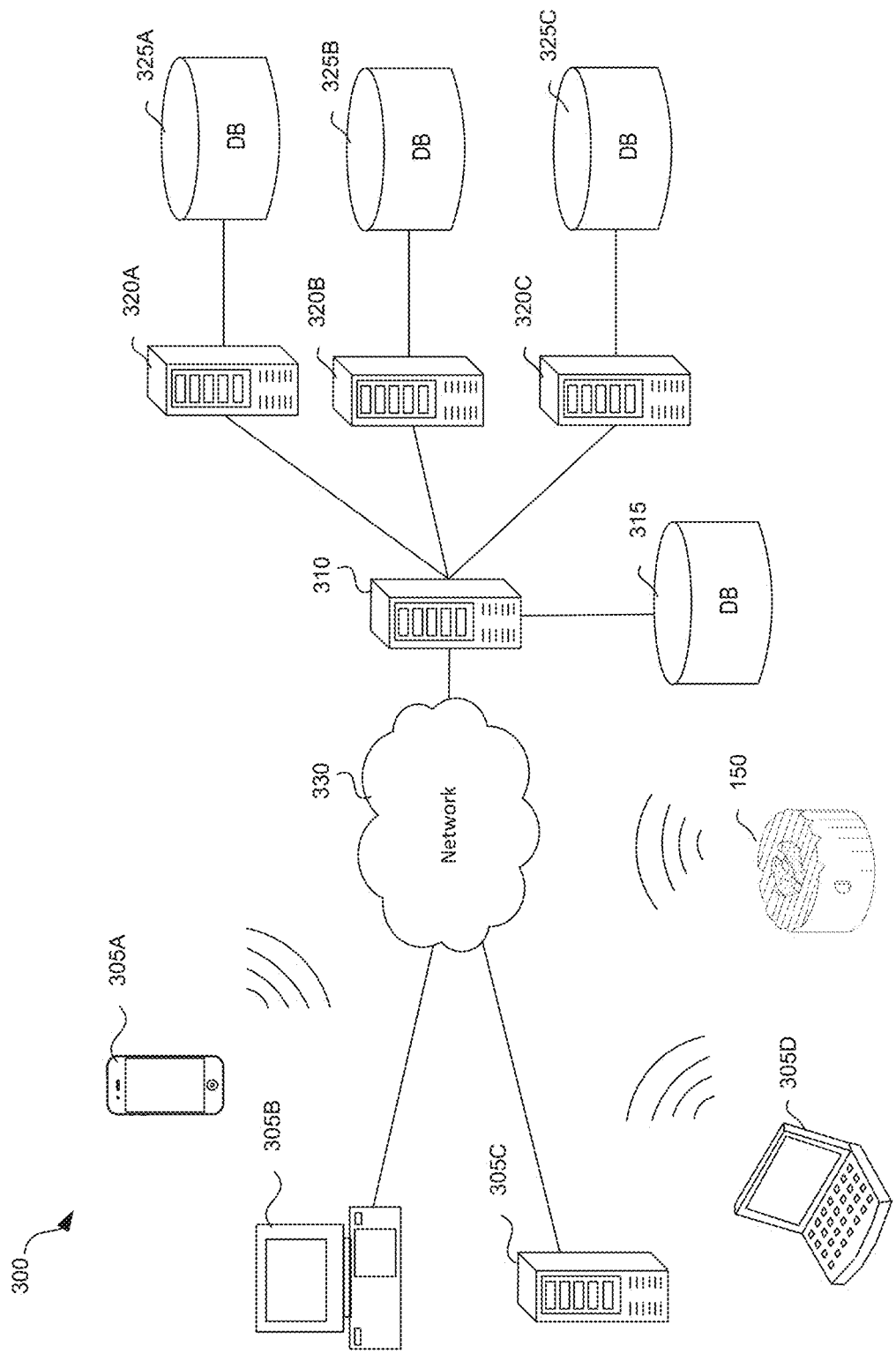
FIG. 3 is a system diagram illustrating an example of a computing environment in which the disclosed system operates in some embodiments.

FIG. 3 is a system diagram illustrating an example of a computing environment in which the disclosed system operates in some embodiments. In some embodiments, environment 300 includes one or more client computing devices 305A-D, examples of which can host the device 200. Client computing devices 305 operate in a networked environment using logical connections through network 330 to one or more remote computers, such as a server computing device. In some implementations, the client computing devices 305 can also include a medical implant, such as the medical implant 150 described above in relation to FIG. 1.

In some embodiments, device 310 is an edge server which receives client requests and coordinates fulfillment of those requests through other servers, such as servers 320A-C. In some embodiments, server computing devices 310 and 320 comprise computing systems, such as the device 200. Though each server computing device 310 and 320 is displayed logically as a single server, server computing devices can each be a distributed computing environment encompassing multiple computing devices located at the same or at geographically disparate physical locations. In some embodiments, each server computing device 320 corresponds to a group of servers.

Client computing devices 305 and server computing devices 310 and 320 can each act as a server or client to other server or client devices. In some embodiments, servers (310, 320A-C) connect to a corresponding database (315, 325A-C). As discussed above, each server 320 can correspond to a group of servers, and each of these servers can share a database or can have its own database. Databases 315 and 325 warehouse (e.g., store) information such as medical information, health records, biometric information of users, blockchain transactions involving user medical records, and other data. In some embodiments, the severs 320A-C can include digital filing cabinets and/or features of other servers disclosed herein, such as server 106 of FIG. 1. Though databases 315 and 325 are displayed logically as single units, databases 315 and 325 can each be a distributed computing environment encompassing multiple computing devices, can be located within their corresponding server, or can be located at the same or at geographically disparate physical locations.

Network 330 can be a local area network (LAN) or a wide area network (WAN) but can also be other wired or wireless networks. In some embodiments, network 330 is the Internet or some other public or private network. Client computing devices 305 are connected to network 330 through a network interface, such as by wired or wireless communication. While the connections between server 310 and servers 320 are shown as separate connections, these connections can be any kind of local, wide area, wired, or wireless network, including network 330 or a separate public or private network.

Figure 4:
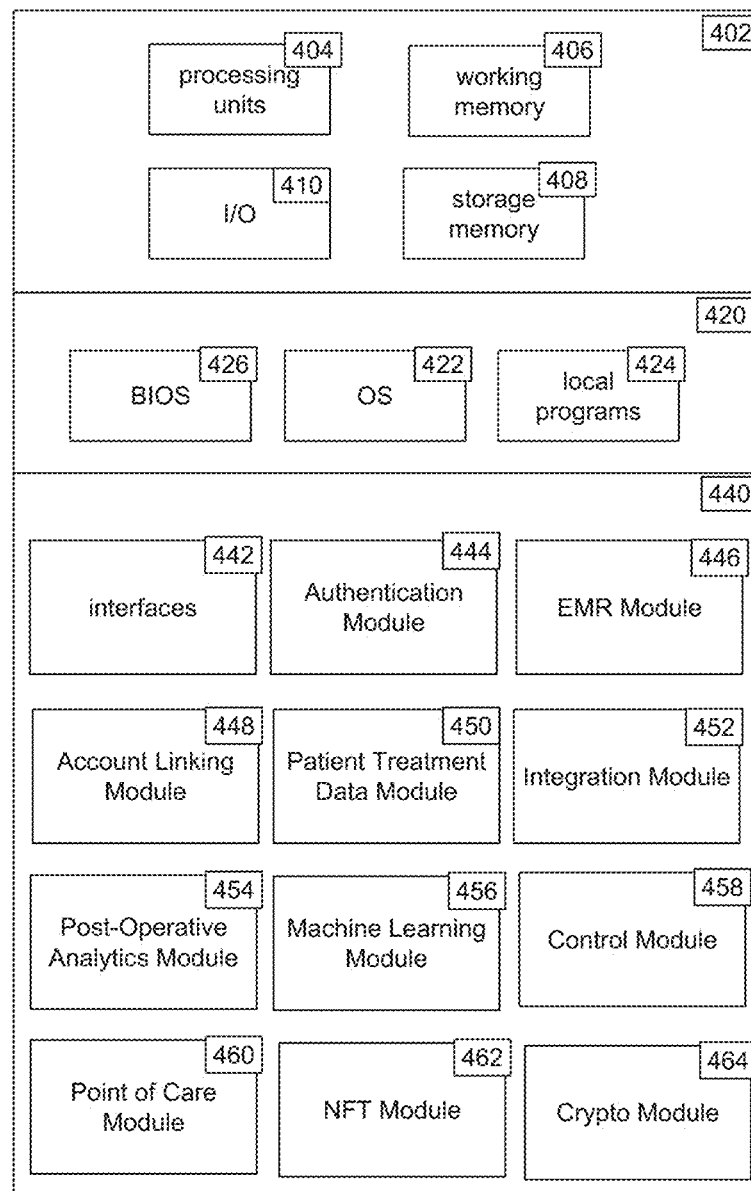
FIG. 4 is a block diagram illustrating components which, in some implementations, can be used in a system employing the disclosed technology.

FIG. 4 is a block diagram illustrating components 400 which, in some implementations, can be used in a system employing the disclosed technology. The components 400 can be used for storing, managing, analyzing, and accessing healthcare data in digital filing cabinets. The components 400 include hardware 402, general software 420, and specialized components 440. As discussed above, a system implementing the disclosed technology can use various hardware including processing units 404 (e.g., CPUs, GPUs, APUs, etc.), working memory 406, storage memory 408 (local storage or as an interface to remote storage, such as storage 315 or 325), and input and output devices 410. In various implementations, storage memory 408 can be one or more of: local devices, interfaces to remote storage devices, or combinations thereof. For example, storage memory 408 can be a set of one or more hard drives (e.g., a redundant array of independent disks (RAID)) accessible through a system bus or can be a cloud storage provider or other network storage accessible via one or more communications networks (e.g., a network accessible storage (NAS) device, such as storage 315 or storage provided through another server 320). Components 400 can be implemented in a client computing device such as client computing devices 305 or on a server computing device, such as server computing device 310 or 320.

General software 420 can include various applications including an operating system 422, local programs 424, and a basic input-output system (BIOS) 426. Specialized components 440 can be subcomponents of a general software application 420, such as local programs 424. Specialized components 440 can be for providing patient-specific healthcare data and can include an authentication module 444, EMR module 446, account linking module 448, patient treatment data module 450, integration module 452, post-operative analytics module 454, machine learning module 456, control module 458, point of care module 460, NFT module 462, crypto module 464 and components which can be used for providing user interfaces, transferring data, and controlling the specialized components, such as interfaces 442 (e.g., user interface on tablet, smartphone, laptop, etc.). In some implementations, components 400 can be in a computing system that is distributed across multiple computing devices or can be an interface to a server-based application executing one or more of specialized components 440. Although depicted as separate components, specialized components 440 may be logical or other nonphysical differentiations of functions and/or may be submodules or code-blocks of one or more applications.

Authentication module 444 provides authentication management of patient-specific healthcare data to users (e.g., patients, family members, healthcare providers, approved users, etc.). Authentication module 444 can manage the access (e.g., read-only, editing capability, privacy protecting, etc.) to the healthcare data based on geolocation, biometrics, blockchain, token (e.g., NFT), or key functionality for user authentication. Authentication module 444 provides token functionality for user authentication to access the healthcare data. Authentication module 444 can generate a token for the user to access medical records. In some implementations, the token is valid for a threshold of time during which the user can access the medical records. A user can request and receive a token from the authentication module 444. In some implementations, authentication module 444 provides key functionality for user authentication to access the healthcare data. The authentication module 444 can share an authentication key (e.g., symmetric or asymmetric key) with the user over a secure channel for the user to access the healthcare data during the time of authentication.

Authentication module 444 provides biometric functionality for user authentication to access the healthcare data. A user can provide their biometric information (e.g., voice, facial scan, fingerprint, iris scanning, dental records, height, weight, etc.) to the authentication module 444. The authentication module 444 can store the biometric information. When the user attempts to access the healthcare data, the authentication module 444 can verify the identity of the user based on the biometric information before granting the user access to medical records. In some cases, the authentication module 444 requires the user to provide two or more types of biometric information, such as a fingerprint and voice, before granting the user access to the medical records.

Authentication module 444 provides geolocation functionality for user authentication to access the healthcare data. Authentication module 444 can verify the location of the user device attempting to access the healthcare data or the location of a patient's device, when determining to permit a user to access healthcare data. In an example, a healthcare provider can only access a patient's medical records at a healthcare facility. In another example, a healthcare provider can only access the patient's medical records when the patient is at the healthcare facility of the healthcare provider.

Authentication module 444 provides blockchain functionality for user authentication to access the healthcare data. The authentication module 444 allows for the creation of a new block for a new/existing blockchain distributed ledger, hashing of the new block, and addition of the new block to the patient's private blockchain and distributed ledger. The authentication module 444 can manage a plurality of public blockchains, private blockchains, and/or other distributed ledgers for patients. In some implementations, the privacy of each patient's blockchain(s) can be ensured because each patient maintains an individual blockchain and/or ledger for the patient's medical records and data. In other implementations, transactions include a public key that matches a private key associated with the patient. In these implementations, while the transactions are added to a public ledger, details of the transactions can only be accessed when the private key is used, ensuring patient data privacy.

New blocks for blockchains and/or ledgers are based on received healthcare data. In some implementations, the created blockchain ledger(s) can be stored in persistent memory of an implant of the patient. In other implementations, the created blockchain ledger(s) can be stored in memory associated with the system and may be a private blockchain ledger associated exclusively with the patient or a public blockchain ledger associated with a group of patients. If the blockchain ledger is a public ledger, each block can be associated with different patients, but cannot be accessed for viewing unless a medical professional possesses a private key associated with the patient identified in a particular block in the ledger. Groups of patients can be subdivided in multiple ways. For example, a group of patients can be defined as all patients at a particular medical facility, all patients under the treatment of a particular medical professional, all patients covered by a particular medical insurance provider, all patients with a similar pathology, treatment, outcome, and the like.

NFT module 462 can convert the healthcare data to one or more NFTs on a blockchain. In some implementations, the healthcare data is converted into multiple NFTs based on the type of data (e.g., medical imaging, billing information, post-operation information, implant information, biometric information, surgery details, personal identifiable information (PII), etc.) and the multiple NFTs are bundled into a single NFT. In some embodiments, the NFT module 462 can analyze data, identify data based on one or more rules, group identified data, and convert grouped data to NFT(s). For example, the NFT module 462 can identify a patient's imaging data or study, a chart or information, surgery information, etc. The NFT module 462 can then covert (1) the patient's imaging data or study into one or more imaging study NFTs, (2) the patient information into one or more patent information NFTs, (3) surgery information in one or more surgery NFTs, etc. For example, the NFT module 462 can generate specific surgical procedure NFTs containing information for their respective surgical procedure. The information contained in or associated with the NFT can be selected by a user. The NFT module 462 can also include a machine learning engine trained to identify, categorize, group, and/or convert data to NFT's. For example, the machine learning model can be trained using healthcare data sets, such as imaging study data sets, EMR data sets, patient information data sets, surgery information data sets, or the like. The machine learning engine can then group data to be contained in or linked to NFTs.

The NFTs can be bundled into one bundling NFT. The bundling NFT can include, for example, one or more imaging study NFTs, patient information NFTs, surgery NFTs, etc. The type and number of NFTs contained by a bundling NFT can be selected by the patient, healthcare provider, etc. In some embodiments, the NFTs are containerized to themselves and can hold EMRs, image data, scans, or other healthcare data disclosed herein. In some embodiments, the NFTs are linked to healthcare data stored off-blockchain using, for example, a decentralized or centralized storage network. The healthcare data can be used to generate metadata of the NFT.

The NFT module 462 can generate non-transferable NFTs and transferable NFTs. Non-transferable NFTs increase security of the healthcare data based on the blockchain properties. For example, the NFTs provide verification of digital healthcare data (e.g., authenticating credentials, preserving data integrity, truth source for patient health records, etc.), ownership of the healthcare data, portability of the healthcare data, patient-specific solutions based on verifiable patient data, patient-specific algorithms for treatment(s), patient-selectable sharing of healthcare data, trackable usages of patient data, economic value (e.g., anonymized, identified, aggregated, partitioned, parsed, grouped, etc.) for use of the healthcare data. NFT module 462 can create transferable NFTs that have rules (e.g., smart contracts) that govern how the NFT is used. For example, the NFT can have an expiration date, indications, require confirmation of the intended recipient, instructions for implantation (by surgical robot), traceable chain of custody (supply chain), authenticity (elimination of counterfeit products), and/or payment (reimbursement) for product (verified, traceable) in cryptocurrency. The NFT module 462 can select or create smart contracts based on user input, healthcare data type, or other criteria. The NFT module 462 can create digital keys for users. For example, private keys for authorizing access to the healthcare data. In some implementations, the digital filing cabinet is a repository for NFTs and digital keys (public and private). Transactions (e.g., accessing, transmitting, receiving, etc.) of the healthcare data can be captured, tracked, and/or authenticated using NFTs. Converting the healthcare data to NFT(s), makes each transaction of the healthcare data completely portable, traceable, protected, and authorized.

Authentication module 444 can authenticate a user with a multi-factor identification, such as requiring two types of authentication from an authentication group which includes blockchain, biometric, token, key, and geolocation types of authentication. Authentication module 444 can adjust the authentication requirements based on the user health metrics. For example, if the user's heart rate is below a threshold level (e.g., indicating the user is experiencing a medical emergency), the authentication module 444 requires lower levels of authentication by a healthcare provider to access the patient's medical records. Adjusting the level of authentication, allows healthcare providers (e.g., surgeon, EMT, etc.) to access medical information while treating the user during the medical emergency. Authentication module 444 can require various levels of security based on the type of medical information in the medical records. For example, health metrics, such as blood pressure or heart rate from a wearable device, require lower authentication levels to access than patient health history or medical insurance information.

EMR module 446 maintains patient electronic medical records. The EMRs can include patient healthcare data (e.g., images, scans, documents, etc.), demographic information about the patient, identifying information of the patient, historical patient treatment data, metrics, plans (e.g., pre-operative plans, corrective plans, surgical plans, post-operative plans, etc.), data providing pathology-related information, provider information (e.g., physician, hospital, surgical team, etc.), patient feedback (e.g., feedback acquired using quality of life questionnaires, surveys, patient-reported outcome measures, etc.), vital signs, diagnostic results, and/or other medically relevant information about the patient, such as family history of various illnesses or medical problems, prescription drug history, and the like. EMR module 446 can also maintain patient treatment records, such as medical procedures undergone, implant information (e.g., patient-specific design, composition, implantation date, manufacture, etc.), drug therapies performed, clinical trials participated in, and other relevant medical actions taken on behalf of the health of the patient. Each medical action can also include various additional data points, such as attending physician, prescribing physician, time and date of action, patient medical reaction, medical action taken, and other relevant medical data points. In some implementations, EMRs can also include various relevant images and scans (e.g., CT scans, 3D CT scans, CMCT scans, MRIs, PET scans, etc.), images (e.g., X-ray images, magnetic resonance imaging, ultrasound images, etc.) associated with medical actions, such as medical images, blood test results, and the like. The EMR module 446 can provide EMRs to the authentication module 444 for generating transactions based on the EMRs. EMR module 446 manages the medical records of the user, such as implant data, surgical plans, health records, or medical insurance information. EMR module 446 can detect updates for the user's medical records and implement the updates into the medical records. For example, EMR module 446 detects a family member is added to the medical insurance plans and updates the medical records to include the additional family member.

Account linking module 448 links the accounts between healthcare providers, family members, banking accounts, credit card accounts, insurance providers, government entities, or any account providing information to the implant (user accounts), healthcare analytic cloud, digital filing cabinet, or healthcare provider. A user (e.g., patient or healthcare provider) can provide authentication credentials (e.g., usernames, passwords, pins, etc.) for their accounts to account linking module 448. In some implementations, account linking module 448 identifies accounts the user needs to provide, such as insurance accounts, healthcare history accounts, or payment accounts, so the system can provide service to the user.

Patient treatment data module 450 gathers patient data regarding a medical event or medical action (e.g., a hospitalization, a medical procedure, a drug therapy regime, and the like) from various medical systems. In one example, patient treatment data module 450 can receive identifying information identifying a patient, a result from a routine physician visit, and any relevant data associated with the visit, such as various medical images taken, blood pressure values, heart rate, blood oxygen levels, body mass index, and/or other medical data. The patient treatment data module 450 can provide this data in an EMR to the EMR module 444 to create new EMRs for patients.

Integration module 452 integrates input sources of patient healthcare data. The input sources can include healthcare data digital filing cabinets, digital wallets, wearable devices, patient implants, health insurance provider devices, healthcare provider devices, cloud-based analytic devices, or patient devices. In some implementations, integration module 452 identifies new healthcare data (e.g., medical charts, medical images, health goals, medical diagnostics, etc.) added to the digital filing cabinet and updates the organized healthcare data with the new healthcare data.

Post-operative analytics module 454 collects and analyses patient information, patient goals, healthcare provider goals for a patient, outcomes of a medical procedure, health metric goals (e.g., BMI, blood pressure, etc.), healthcare provider notes from procedures or patient exams, etc. For example, after a medical procedure, the post-operative analytics module 454 analyzed x-ray images to determine whether the medical procedure was successful. The post-operative analytics module 454 can determine whether the patient should attend physical therapy based on collected health metrics, such as patient mobility (e.g., range of motion of limbs or fingers). The post-operative analytics module 454 can identify EMRs that a healthcare provider should review, such as new spots in an MRI which can indicate cancer. In some implementations, the post-operative analytics are converted to an NFT.

Machine learning module 456 may be configured to analyze user healthcare data in a digital filing cabinet to determine to notify the events (e.g., emergencies, appointments, health goals, etc.). The machine learning module 456 may be configured to analyze healthcare data based on at least one machine-learning algorithm trained on at least one dataset reflecting a user's healthcare information, goals, and health status. The at least one machine-learning algorithms (and models) may be stored locally at databases and/or externally at databases (e.g., cloud databases and/or cloud servers). Client devices may be equipped to access these machine learning algorithms and intelligently analyze healthcare data and notify a user based on at least one machine learning model that is trained on a user's historical healthcare data. For example, if a user frequently has increased blood sugar levels, the user's health metrics may be collected to train a machine learning model to then automatically notify the user to exercise to help lower the user's blood sugar.

As described herein, a machine-learning (ML) model may refer to a predictive or statistical utility or program that may be used to determine a probability distribution over one or more character sequences, classes, objects, result sets or events, and/or to predict a response value from one or more predictors. A model may be based on, or incorporate, one or more rule sets, machine learning, a neural network, or the like. In examples, the ML models may be located on the client device, service device, a network appliance (e.g., a firewall, a router, etc.), or some combination thereof. The ML models may process user healthcare data and other data stores of user health metrics to determine when to generate a notification for a user. Based on an aggregation of data from a user's healthcare digital filing cabinet, wearable devices, and other user data stores, at least one ML model may be trained and subsequently deployed to automatically generate healthcare notifications. The trained ML model may be deployed to one or more devices. As a specific example, an instance of a trained ML model may be deployed to a server device and to a client device. The ML model deployed to a server device may be configured to be used by the client device when, for example, the client device is connected to the Internet. Conversely, the ML model deployed to a client device may be configured to be used by the client device when, for example, the client device is not connected to the Internet. In some instances, a client device may not be connected to the Internet but still configured to receive satellite signals with healthcare data. In such examples, the ML model may be locally cached by the client device. In some implementations, the machine learning module 456 identifies new healthcare data in the digital filing cabinet and updates the health goals or metrics of the patient based on the new healthcare data.

Control module 458 controls the patient healthcare data in the healthcare provider digital filing cabinet. The control module 458 can determine automated settings for searching, periodically or continually, for additional data to add to the digital filing cabinet. Control module 458 can manage the privacy of the healthcare data by requiring authentication credentials (as described in authentication module 444) of any user attempting to access the patient healthcare data. In some implementations, the control module 458 encrypts the patient healthcare data. Control module 458 can identify new healthcare data and update the digital filing cabinet of the healthcare provider to include the new healthcare data.

Point of care (POC) module 460 identifies POC devices, such as healthcare provider devices (e.g., medical instruments, charting devices, patient monitoring devices, etc.) or patient devices (e.g., wearable devices, implants, smartphones, etc.) and retrieves collected data from POC devices. The POC module 460 can collect health history data, treatment data, health metrics of the patient, the geolocation of the patient, insurance information, biometric data, or payment information from the POC devices. The POC module 460 can display versions of the health data on a user device for a healthcare provider to show a patient. For example, the POC module 460 displays x-ray images on a user interface so the patient can see an implant after a surgery procedure. POC module 460 provides alerts based on events identified from healthcare data inputted into a digital filing cabinet. For example, the alerts are user (e.g., physician, Doctor, patient etc.) notifications from monitoring data collected from wearable devices. The POC module 460 can generate an alert to request additional or updated patient information, scheduling appointments, notifying of emergencies, etc. For example, the POC module 460 can generate an alert when the patient's health metrics (e.g., heart rate, blood pressure, body temperature, etc.) are outside of healthy metric threshold (e.g., a threshold or range determined by a healthcare provider).

Crypto module 464 can charge cryptocurrency for each transaction of an NFT. Examples of a transaction (or transaction steps) can include imaging (e.g., MRIs, X-rays, radiology imaging) converted to an NFT(s), patient information (e.g., height, weight, gender, health status, etc.) converted to NFT(s), surgery details (e.g., date of surgery, surgical team, instrument information, implant information, physician information, etc.) converted to NFT(s), bundling of NFTs, transmission of NFT(s) to a recipient for devising a surgical plan, create surgical plan in NFT(s), transmission of surgical plan NFT(s) to a healthcare provider (e.g., doctor, hospital, clinic, surgeon, etc.), transmission of approval of plan using NFT(s), create implant design in NFT(s), transmission of implant design NFT(s) to a manufacturing company, manufacture implant based on implant design NFT(s), shipping physical implant to surgery, post-operative data collected and converted to NFT, and/or transmission of post-op data NFT(s) to recipient for incorporation into feedback for the next correction and implant design. The NFTs can include lockable content (e.g., patient healthcare data), unlockable content (e.g., healthcare provider contact information), etc. The crypto module 464 can create a crypto coin for transactions of the NFTs of the healthcare data. The NFTs, crypto coins, and digital keys can be stored in a digital wallet.

Figure 5:
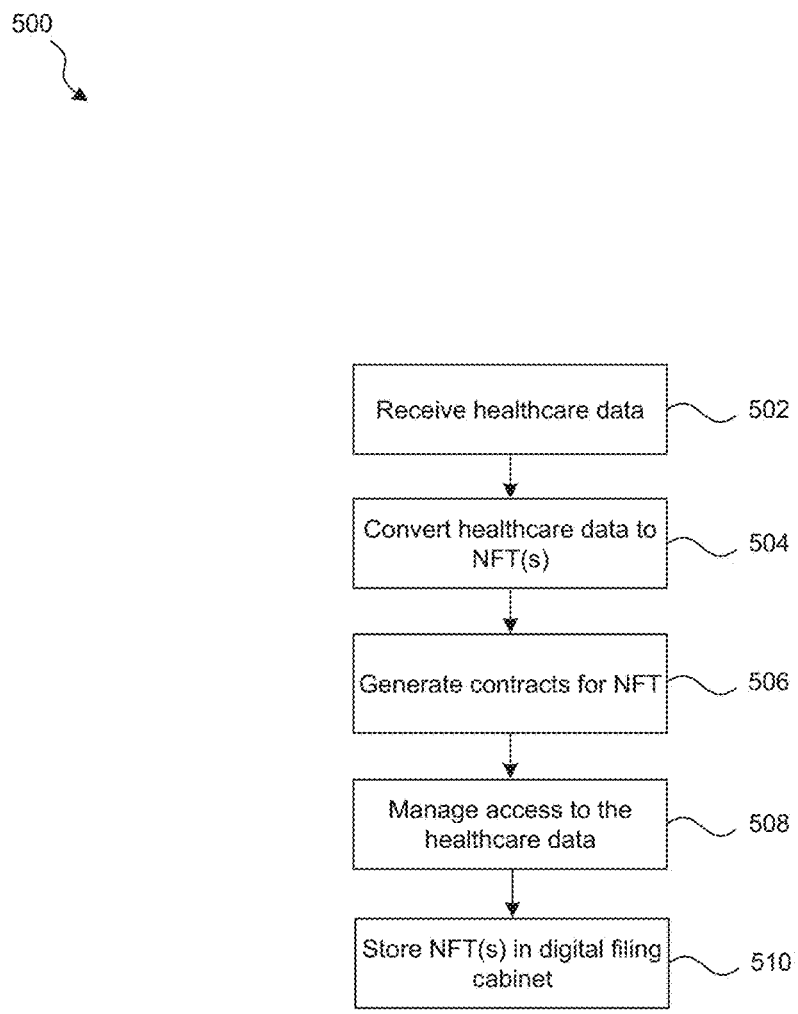
FIG. 5 is a flow diagram illustrating a process used in some implementations for converting patient-specific healthcare data into a non-fungible token.

FIG. 5 is a flow diagram illustrating a process 500 for converting patient-specific healthcare data into a non-fungible token, according to an embodiment. At step 502, process 500 can receive the healthcare data from multiple entities (e.g., healthcare providers, hospitals, medical clinics, insurance companies, patient social media accounts, patients, etc.) and store the healthcare data in a digital filing cabinet. In some implementations, the digital filing cabinet is in an implant in a patient. In some implementations, the digital filing cabinet is located at cloud-based devices, storage devices, healthcare provider devices, and/or patient devices. A patient can provide authentication credentials (e.g., usernames, passwords, etc.) for the accounts providing data to the digital filing cabinet. The healthcare data (e.g., EMRs) can include data representative of the patient's condition, anatomy, pathology, symptoms, medical history, preferences, and/or any other information or parameters relevant to the patient. For example, the healthcare data can include surgical intervention data, treatment outcome data, progress data (e.g., surgeon notes), patient feedback (e.g., feedback acquired using quality of life questionnaires, surveys), clinical data, patient information (e.g., demographics, sex, age, height, weight, type of pathology, occupation, activity level, tissue information, health rating, comorbidities, health related quality of life (HRQL)), vital signs, diagnostic results, medication information, allergies, diagnostic equipment information (e.g., manufacturer, model number, specifications, user-selected settings/configurations, etc.) or the like. The healthcare data can also include image data, such as camera images, Magnetic Resonance Imaging (MRI) images, ultrasound images, Computerized Aided Tomography (CAT) scan images, Positron Emission Tomography (PET) images, X-Ray images, and the like. In some embodiments, the healthcare data includes data representing one or more of patient identification number (ID), age, gender, body mass index (BMI), lumbar lordosis, Cobb angle(s), pelvic incidence, disc height, segment flexibility, bone quality, rotational displacement, and/or treatment level of the spine. The healthcare data can include implant information (e.g., dimensions, material, design, etc.) for an implant for a patient. The healthcare data can be received at a server, computing device, or other computing system. For example, in some embodiments the patient data set can be received by the server 106 shown in FIG. 1. The computing system that receives the healthcare data in step 502 can also store one or more software modules (e.g., the data analysis module 116 shown in FIG. 1, or additional software modules for performing various operations of the process 500).

At step 504, process 500 converts the healthcare data into NFTs. Process 500 can generate a digital key (private and public) to access each NFT and a digital wallet(s). A user can "unlock" an NFT with the digital key. The digital wallet(s) can be repositories for NFTs, crypto coins, and digital keys. Process 500 can issue the digital wallets and keys to users. In an example, process 500 issues a digital wallet to a patient with a private key for authorizing access to the healthcare data in an NFT. In another example, process 500 issues digital wallets to a hospital with a public key for authorizing access to the healthcare data in the NFT. In another example, process 500 issues a digital wallet to a surgeon with a public key for authorizing access to the healthcare data in the NFT and a private key for authorizing surgeon-specific access to the healthcare data in the NFT. In some embodiments, the process 500 tokenizes the healthcare data into NFTs by determining a storage location for the healthcare data and generating an NFT-linked to the healthcare data. The link type (e.g., URL, interplanetary file system link, etc.) can be selected based on the storage timeframe and costs. The NFT can include metadata with the link(s). This allows the healthcare data or linking to be transferred with the NFTs.

At step 506, process 500 generates access parameters (e.g., smart contract, authentication level from authentication module 444 of FIG. 4, etc.) for each NFT. For example, the access parameters can limit the number of times (e.g., one-time use, threshold number of times, etc.) the NFT can be accessed by a user. In some implementations, the NFT has an expiration date, and a user can only access the NFT prior to the expiration date. For example, if an NFT of an implant design for a patient is sent to a manufacturer, the access parameters of the NFT can restrict the manufacturer to a date to view the implant design before the NFT expires. Access parameters can protect the implant design by ensuring that the manufacturer is the only one who can access the NFT. The access parameters can include additional features such as the geolocation of the user, device of the user, biometrics, or other authentication credentials. For example, for a healthcare provider to access an NFT containing patient healthcare data, process 500 requires the healthcare provider to provide the digital key and verifies the healthcare provider is at a healthcare provider location.

At step 508, process 500 manages access to the healthcare data associated with (e.g., linked to, part of, etc.) the NFT(s) according to the access parameters. A user can provide the digital key (public and/or private) to access the healthcare data, and in some cases biometric data, geolocation data, or other types of authentication to access the healthcare data. At step 510, process 500 stores the NFT in a digital wallet. Digital wallet can be stored in the digital filing cabinet.

Figure 6:
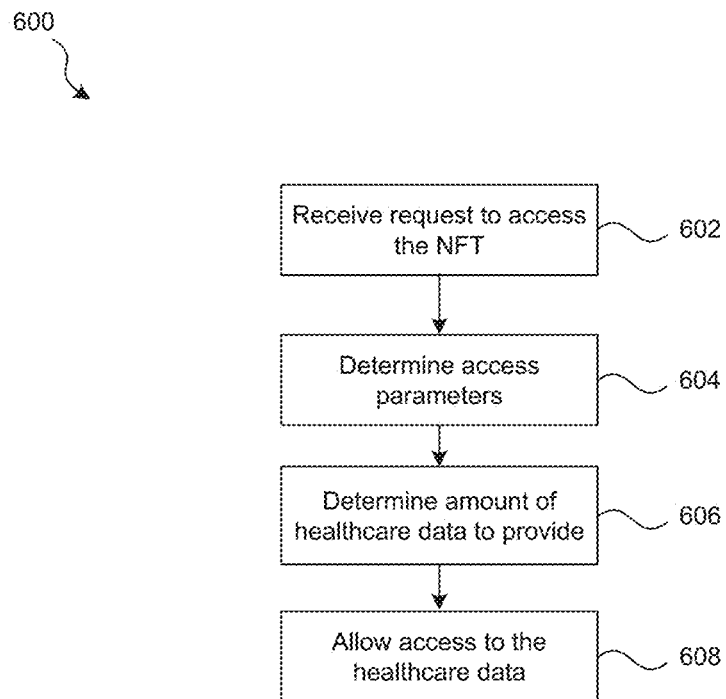
FIG. 6 is a flow diagram illustrating a process used in some implementations for providing patient-specific healthcare data from an implant.

FIG. 6 is a flow diagram illustrating a process 600 for managing access to patient-specific healthcare data from an implant, according to an embodiment. At step 602, process 600 receives a request, from a user (e.g., patient, healthcare provider, insurance representative, implant manufacturer, etc.), to access an NFT containing healthcare data. For example, a user can scan an implant in a patient's body or access the NFT via a blockchain network device. A user can provide authorization credentials (e.g., password, passphrase, token, security push code, etc.) to access the private key. Based on the patient authorization credentials, process 600 can allow the user access to the private key stored on the blockchain-enabled medical implant.

At step 604, process 600 determines the access parameters of the NFT for the user. In some implementations, the user can access the healthcare data in the NFT with a digital key. In some implementations, process 600 requires the user provide a digital key in addition to geolocation data, biometric data, or other authentication credentials before granting the user access to the healthcare data.

At step 606, process 600 determines the amount of healthcare data to provide based on the user and access parameters. Based on the user and access parameters, the user is granted read-only capabilities, editing capabilities, or the capability to view all or some of the healthcare data. For example, a patient can view all their own healthcare data and personal information (e.g., SSN, banking information, insurance information, etc.) but a healthcare provider is limited to patient health history information. In some implementations, the location of the patient (e.g., determined via the implant location) can determine the access parameters of the NFT. For example, if a patient is in an accident in a foreign country, a healthcare provider can only access emergency contact information or specific emergency medical information (e.g., blood type, allergies, medication, etc.) from the NFT. However, if the healthcare provider is the patient's primary healthcare provider (proven by biometrics), the healthcare provider has a different level of access to the healthcare data than another healthcare provider.

At step 608, process 600 allows the user to access the healthcare data based on the access parameters of the NFT. The implant can include a wireless chip (e.g., Bluetooth chip or Near Field Communication (NFC) chip) so that the user interface can wirelessly receive the healthcare data. Process 600 can transmit the healthcare data in an encrypted format and the user can decrypt the healthcare data. In some implementations, process 600 can generate and transmit a code (e.g., QR, RFID, etc.) that a user can scan to access healthcare data on the implant. In some implementations, process 600 denies the user access to the NFT.

The systems/devices 100, 200, 300, 400 can perform one or more steps of the methods discussed in connection with FIGS. 5-6. For example, the systems and components can perform various steps and methods described in connection with FIGS. 5-6 in other steps and methods disclosed herein. Thus, although certain operations are discussed in connection with FIGS. 5-6 for specific components, other components and systems disclosed herein can be incorporated into or operate with the other components disclosed herein.

FIG. 7 illustrates an example of a healthcare data set 700 (e.g., as received in step 502 of FIG. 5) that can be converted to an NFT(s). The healthcare data 700 can include any of the information previously described with respect to healthcare data. For example, the healthcare data includes patient information (e.g., patient identification no., patient MRN, patient name, sex, age, body mass index (BMI), surgery date, surgeon, etc.), diagnostic information (e.g., Oswestry Disability Index (ODI), VAS-back score, VAS-leg score, Pre-operative pelvic incidence, pre-operative lumbar lordosis, pre-operative PI-LL angel, pre-operative lumbar coronal cobb, etc.), and image data 702 (x-ray, CT, MRI, etc.)

Figure 8:
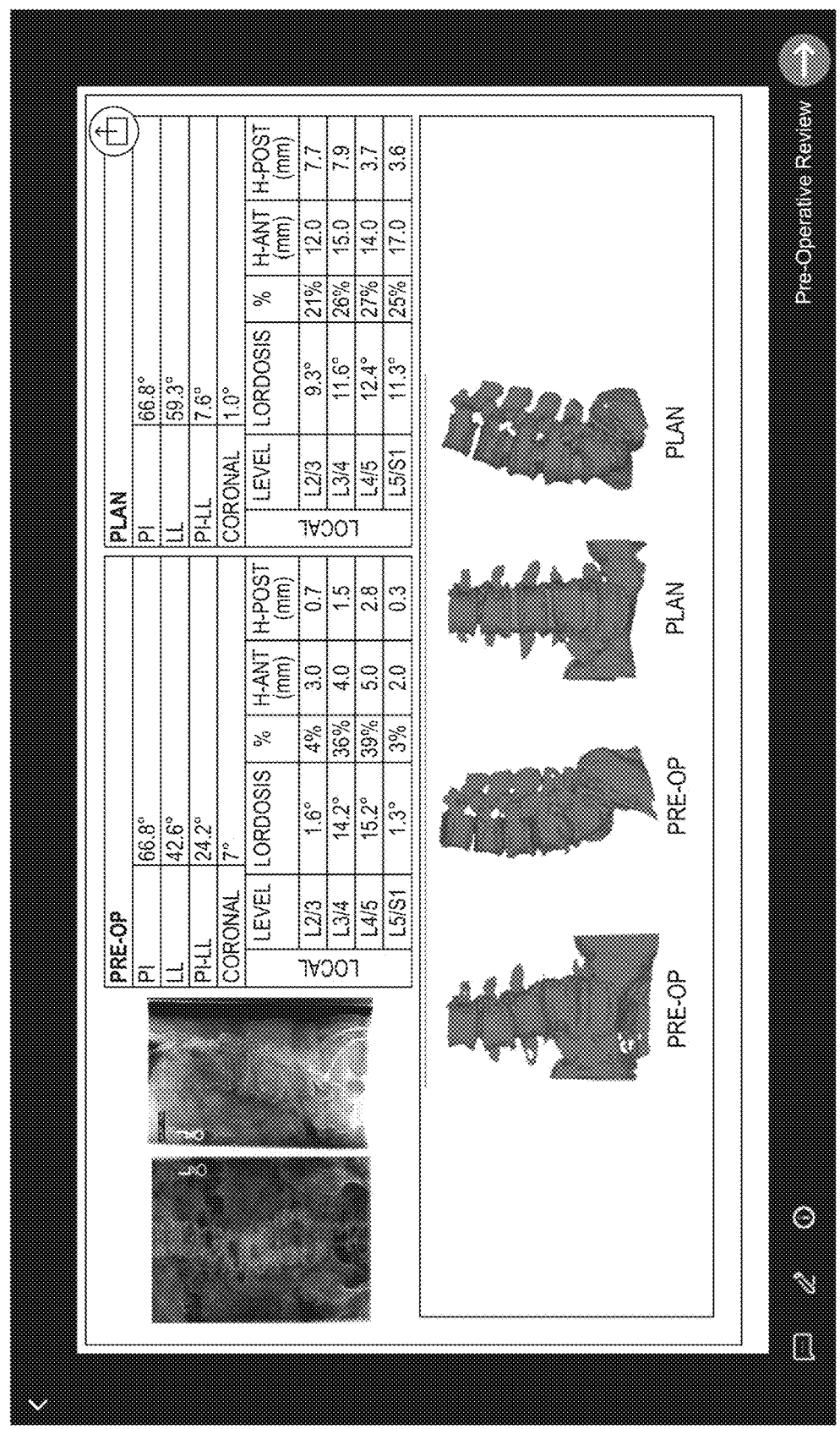
FIG. 8 illustrates an exemplary surgical plan report that may be used and/or generated in connection with the methods described herein, according to an embodiment.

FIG. 8 provides a series of images illustrating an example of a patient surgical plan report 800 that may be converted on an NFT and transmitted to a patient. The surgical plan report 800 can include an overview of a surgical plan, patient images, patient metrics, surgical details, and related information that the patient can view. The patient surgical plan report 800 can be presented to the patient on a digital display of a computing device (e.g., the client computing device 102 shown in FIG. 1). In some embodiments, the report 800 is interactive and the patient can manipulate various aspects of the report 800 (e.g., adjust views, zoom-in, zoom-out, annotate, etc.). The patient may provide questions or comments for the healthcare provider, which can be sent back to the computing system that generated the surgical plan report 800 for analysis and answers.

As one skilled in the art will appreciate, any of the software modules described previously may be combined into a single software module for performing the operations described herein. Likewise, the software modules can be distributed across any combination of the computing systems and devices described herein, and are not limited to the express arrangements described herein. Accordingly, any of the operations described herein can be performed by any of the computing devices or systems described herein, unless expressly noted otherwise.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In some embodiments, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected," or "operably coupled," to each other to achieve the desired functionality, and any two components capable of being so associated can also be viewed as being "operably couplable" to each other to achieve the desired functionality. Specific examples of operably couplable include but are not limited to physically mateable and/or physically interacting components and/or wirelessly interactable and/or wirelessly interacting components and/or logically interacting and/or logically interactable components.

The embodiments, features, systems, devices, materials, methods and techniques described herein may, in some embodiments, be similar to any one or more of the embodiments, features, systems, devices, materials, methods and techniques described in the following:

- U.S. application Ser. No. 16/048,167, filed on Jul. 27, 2017, titled "SYSTEMS AND METHODS FOR ASSISTING AND AUGMENTING SURGICAL PROCEDURES";
- U.S. application Ser. No. 16/242,877, filed on Jan. 8, 2019, titled "SYSTEMS AND METHODS OF ASSISTING A SURGEON WITH SCREW PLACEMENT DURING SPINAL SURGERY";
- U.S. application Ser. No. 16/207,116, filed on Dec. 1, 2018, titled "SYSTEMS AND METHODS FOR MULTI-PLANAR ORTHOPEDIC ALIGNMENT";
- U.S. application Ser. No. 16/352,699, filed on Mar. 13, 2019, titled "SYSTEMS AND METHODS FOR ORTHOPEDIC IMPLANT FIXATION";
- U.S. application Ser. No. 16/383,215, filed on Apr. 12, 2019, titled "SYSTEMS AND METHODS FOR ORTHOPEDIC IMPLANT FIXATION";
- U.S. application Ser. No. 16/569,494, filed on Sep. 12, 2019, titled "SYSTEMS AND METHODS FOR ORTHOPEDIC IMPLANTS";
- U.S. Application No. 62/773,127, filed on Nov. 29, 2018, titled "SYSTEMS AND METHODS FOR ORTHOPEDIC IMPLANTS";
- U.S. Application No. 62/928,909, filed on Oct. 31, 2019, titled "SYSTEMS AND METHODS FOR DESIGNING ORTHOPEDIC IMPLANTS BASED ON TISSUE CHARACTERISTICS";
- U.S. application Ser. No. 16/735,222, filed Jan. 6, 2020, titled "PATIENT-SPECIFIC MEDICAL PROCEDURES AND DEVICES, AND ASSOCIATED SYSTEMS AND METHODS";
- U.S. application Ser. No. 16/987,113, filed Aug. 6, 2020, titled "PATIENT-SPECIFIC ARTIFICIAL DISCS, IMPLANTS AND ASSOCIATED SYSTEMS AND METHODS";
- U.S. application Ser. No. 16/990,810, filed Aug. 11, 2020, titled "LINKING PATIENT-SPECIFIC MEDICAL DEVICES WITH PATIENT-SPECIFIC DATA, AND ASSOCIATED SYSTEMS, DEVICES, AND METHODS";
- U.S. application Ser. No. 17/463,054, filed Aug. 31, 2021, titled "BLOCKCHAIN MANAGED MEDICAL IMPLANTS;"
- U.S. application Ser. No. 17/085,564, filed Oct. 30, 2020, titled "SYSTEMS AND METHODS FOR DESIGNING ORTHOPEDIC IMPLANTS BASED ON TISSUE CHARACTERISTICS"; and
- U.S. application Ser. No. 17/100,396, filed Nov. 20, 2020, titled "PATIENT-SPECIFIC VERTEBRAL IMPLANTS WITH POSITIONING FEATURES."

All of the patents and applications referenced herein are incorporated by reference in their entireties. In addition, the embodiments, features, systems, devices, materials, methods, and techniques described herein may, in certain embodiments, be applied to or used in connection with any one or more of the embodiments, features, systems, devices, or other matter.

The ranges disclosed herein also encompass any and all overlap, sub-ranges, and combinations thereof. Language such as "up to," "at least," "greater than," "less than," "between," or the like includes the number recited. Numbers preceded by a term such as "approximately," "about," and "substantially" as used herein include the recited numbers (e.g., about 10%=10%), and also represent an amount close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of the stated amount.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

What is claimed is:

1. A blockchain-enabled medical implant, comprising:
 a physical body configured to be implanted within a patient;
 a proximity communication component physically coupled to the physical body; and
 a memory operatively coupled to the proximity communication component, the memory storing a private key that is provide via the proximity communication component to an external device for enabling the external device to access one or more electronic medical records associated with the patient from a distributed blockchain ledger of electronic medical records, wherein the memory stores instructions to:
  establish communicative contact with the external device using a proximity communication mode; and
  allow access, based on an authentication level, to the private key to access a patient-specific healthcare data in at least one non-fungible token.

2. The blockchain-enabled medical implant of claim 1, wherein the blockchain-enabled medical implant is a pedicle screw, an interbody implant system, an artificial disc, an expandable intervertebral implant, a sacroiliac implant, a plate, an arthroplasty device for orthopedic joints, a non-structural implant, a patient-specific implant, or a multipurpose implant.

3. The blockchain-enabled medical implant of claim 1, wherein the memory further stores one or more electronic medical records associated with the patient.

4. A blockchain-enabled medical implant, comprising:
 a physical body configured to be implanted within a patient;
 a proximity communication component physically coupled to the physical body; and
 a memory operatively coupled to the proximity communication component, the memory storing a private key that is provide via the proximity communication component to an external device for enabling the external device to access one or more electronic medical records associated with the patient from a distributed blockchain ledger of electronic medical records;
 one or more sensors configured to measure pressures, loads, or forces applied by anatomical elements of the patient to the medical implant; and
 one or more processors operably coupled to the memory and configured to perform a process comprising:
  receiving data from the one or more sensors;
  determining one or more of an activity level, activities performed, or disease progression based on the received data; and
  communicating, by the proximity communication component, the one or more of the activity level, activities performed, or disease progression to the external device or an external computing system.

5. A system comprising:
a blockchain-enabled medical implant comprising
a physical body configured to be implanted within a patient,
a proximity communication component physically coupled to the physical body, and
a memory operatively coupled to the proximity communication component, the memory storing a private key that is provide via the proximity communication component to an external device for enabling the external device to access one or more electronic medical records associated with the patient from a distributed blockchain ledger of electronic medical records; and
a secondary implant comprising a second proximity communication component that communicates with the proximity communication component and one or more external computing devices.

6. The blockchain-enabled medical implant of claim 5, wherein the medical implant is a blockchain-enabled orthopedic implant and the secondary implant is a digital implant.

7. A blockchain-enabled medical implant, comprising:
a physical body configured to be implanted within a patient;
a proximity communication component physically coupled to the physical body; and
a memory operatively coupled to the proximity communication component, the memory storing
a private key that is provide via the proximity communication component to an external device for enabling the external device to access one or more electronic medical records associated with the patient from a distributed blockchain ledger of electronic medical records, and
a private distributed ledger of transactions associated with medical records of the patient.

8. A method for managing an electronic medical record for a patient, the method comprising:
receiving patient treatment information associated with a patient;
generating an electronic medical record of the patient;
generating a blockchain transaction based on the electronic medical record, a public key, and a private key, wherein
the public key and the private key are a matching pair,
the private key is configured for accessing one or more details of the blockchain transaction and is associated with a blockchain-enabled medical implant for the patient, and
the private key is stored by the blockchain-enabled medical implant; and
adding the blockchain transaction to a distributed ledger of transactions associated with the patient, wherein the blockchain transaction is added to a private ledger or as a private transaction to a public ledger; and
associating the public key and the private key with a unique patient identifier for the patient.

9. A method for managing an electronic medical record for a patient, the method comprising:
receiving patient treatment information associated with a patient;
generating an electronic medical record of the patient;
generating a blockchain transaction based on the electronic medical record, a public key, and a private key, wherein
the public key and the private key are a matching pair,
the private key is configured for accessing one or more details of the blockchain transaction and is associated with a blockchain-enabled medical implant for the patient, and
the private key is stored by the blockchain-enabled medical implant;
adding the blockchain transaction to a distributed ledger of transactions associated with the patient, wherein the blockchain transaction is added to a private ledger or as a private transaction to a public ledger;
establishing communicative contact with the blockchain-enabled medical implant using a proximity communication mode;
accessing, based on an authentication level, the private key; and
accessing patient-specific healthcare data in at least one non-fungible token associated with the private key.

10. A method for managing an electronic medical record for a patient, the method comprising:
receiving patient treatment information associated with a patient, wherein the patient treatment information includes patient data, one or more medical images associated with the patient, one or more scans associated with the patient, demographic information about the patient, identifying information of the patient, historical patient treatment data, metrics, patient treatment plans, data providing pathology-related information of the patient, provider, patient feedback data, vital signs, diagnostic results, patient family history of illnesses or medical problems, and/or prescription drug history of the patient;
generating an electronic medical record of the patient;
generating a blockchain transaction based on the electronic medical record, a public key, and a private key, wherein
the public key and the private key are a matching pair,
the private key is configured for accessing one or more details of the blockchain transaction and is associated with a blockchain-enabled medical implant for the patient, and
the private key is stored by the blockchain-enabled medical implant; and
adding the blockchain transaction to a distributed ledger of transactions associated with the patient, wherein the blockchain transaction is added to a private ledger or as a private transaction to a public ledger.

11. A method for managing an electronic medical record for a patient, the method comprising:
receiving patient treatment information associated with a patient;
generating an electronic medical record of the patient, wherein the electronic medical record includes information associated with a physician delivering treatment to the patient and/or information associated with a facility providing treatment to the patient;
generating a blockchain transaction based on the electronic medical record, a public key, and a private key, wherein
the public key and the private key are a matching pair,
the private key is configured for accessing one or more details of the blockchain transaction and is associated with a blockchain-enabled medical implant for the patient, and
the private key is stored by the blockchain-enabled medical implant; and
adding the blockchain transaction to a distributed ledger of transactions associated with the patient, wherein the blockchain transaction is added to a private ledger or as a private transaction to a public ledger.

12. A method for managing an electronic medical record for a patient, the method comprising:
   receiving patient treatment information associated with a patient;
   generating an electronic medical record of the patient;
   generating a blockchain transaction based on the electronic medical record, a public key, and a private key, wherein
      the public key and the private key are a matching pair,
      the private key is configured for accessing one or more details of the blockchain transaction and is associated with a blockchain-enabled medical implant for the patient, and
      the private key is stored by the blockchain-enabled medical implant; and
   adding the blockchain transaction to a distributed ledger of transactions associated with the patient, wherein the blockchain transaction is added to a private ledger or as a private transaction to a public ledger, wherein the distributed ledger of transactions is the private ledger of transactions associated with the patient, and wherein the private key is required to access the distributed ledger of transactions.

13. The method of claim 12, wherein the distributed ledger of transactions is stored at least partly in memory of the blockchain-enabled medical implant.

14. A method for managing an electronic medical record for a patient, the method comprising:
   receiving patient treatment information associated with a patient;
   generating an electronic medical record of the patient;
   generating a blockchain transaction based on the electronic medical record, a public key, and a private key, wherein
      the public key and the private key are a matching pair,
      the private key is configured for accessing one or more details of the blockchain transaction and is associated with a blockchain-enabled medical implant for the patient, and
      the private key is stored by the blockchain-enabled medical implant; and
   adding the blockchain transaction to a distributed ledger of transactions associated with the patient, wherein the blockchain transaction is added to a private ledger or as a private transaction to a public ledger, wherein the distributed ledger of transactions is the public ledger of transactions, and wherein the private key is used to access transactions associated with the patient stored on the public ledger of transactions.

15. A method for managing an electronic medical record for a patient, the method comprising:
   receiving patient treatment information associated with a patient;
   generating an electronic medical record of the patient, wherein the electronic medical record includes one or more permissions defining one or more portions of the electronic medical record accessible by a particular user;
   generating a blockchain transaction based on the electronic medical record, a public key, and a private key, wherein
      the public key and the private key are a matching pair,
      the private key is configured for accessing one or more details of the blockchain transaction and is associated with a blockchain-enabled medical implant for the patient, and
      the private key is stored by the blockchain-enabled medical implant; and
   adding the blockchain transaction to a distributed ledger of transactions associated with the patient, wherein the blockchain transaction is added to a private ledger or as a private transaction to a public ledger.

16. A non-transitory computer-readable medium storing instructions that, when executed by a computing system, cause the computing system to perform operations comprising:
   receiving patient treatment information associated with a patient;
   generating an electronic medical record of the patient;
   generating a blockchain transaction based on the electronic medical record, a public key and a private key, wherein
      the public key and the private key are a matching pair,
      the private key configured for accessing one or more details of the blockchain transaction and is associated with a blockchain-enabled medical implant, and
      the private key is stored by a blockchain-enabled medical implant in the patient; and
   adding the blockchain transaction to a distributed ledger of transactions associated with the patient, wherein the blockchain transaction is added to a private ledger or as a private transaction to a public ledger; and
   associating the public key and the private key with a unique patient identifier for the patient.

17. The non-transitory computer-readable medium of claim 16, wherein the distributed ledger of transactions is the public ledger of transactions, and wherein the private key associated with the patient is used to access transactions associated with the patient stored on the public ledger of transactions.

18. A non-transitory computer-readable medium storing instructions that, when executed by a computing system, cause the computing system to perform operations comprising:
   receiving patient treatment information associated with a patient;
   generating an electronic medical record of the patient;
   generating a blockchain transaction based on the electronic medical record, a public key and a private key, wherein
      the public key and the private key are a matching pair,
      the private key configured for accessing one or more details of the blockchain transaction and is associated with a blockchain-enabled medical implant, and
      the private key is stored by a blockchain-enabled medical implant in the patient;
   adding the blockchain transaction to a distributed ledger of transactions associated with the patient, wherein the blockchain transaction is added to a private ledger or as a private transaction to a public ledger;
   establishing communicative contact with the blockchain-enabled medical implant using a proximity communication mode;
   accessing, based on an authentication level, the private key; and
   accessing patient-specific healthcare data in at least one non-fungible token associated with the private key.

19. A non-transitory computer-readable medium storing instructions that, when executed by a computing system, cause the computing system to perform operations comprising:
- receiving patient treatment information associated with a patient;
- generating an electronic medical record of the patient;
- generating a blockchain transaction based on the electronic medical record, a public key and a private key, wherein
  - the public key and the private key are a matching pair,
  - the private key configured for accessing one or more details of the blockchain transaction and is associated with a blockchain-enabled medical implant, and
  - the private key is stored by a blockchain-enabled medical implant in the patient; and
- adding the blockchain transaction to a distributed ledger of transactions associated with the patient, wherein the blockchain transaction is added to a private ledger or as a private transaction to a public ledger, wherein the distributed ledger of transactions is the private ledger of transactions associated with the patient, and wherein the private key is required to access the distributed ledger of transactions.

20. A non-transitory computer-readable medium storing instructions that, when executed by a computing system, cause the computing system to perform operations comprising:
- receiving patient treatment information associated with a patient;
- generating an electronic medical record of the patient;
- generating a blockchain transaction based on the electronic medical record, a public key and a private key, wherein
  - the public key and the private key are a matching pair,
  - the private key configured for accessing one or more details of the blockchain transaction and is associated with a blockchain-enabled medical implant, and
  - the private key is stored by a blockchain-enabled medical implant in the patient; and
- adding the blockchain transaction to a distributed ledger of transactions associated with the patient, wherein the blockchain transaction is added to a private ledger or as a private transaction to a public ledger, wherein the distributed ledger of transactions is stored in memory of the blockchain-enabled medical implant.

21. A non-transitory computer-readable medium storing instructions that, when executed by a computing system, cause the computing system to perform operations comprising:
- receiving patient treatment information associated with a patient;
- generating an electronic medical record of the patient, wherein the electronic medical record further includes one or more permissions defining one or more portions of the medical record that can be accessed by a particular user;
- generating a blockchain transaction based on the electronic medical record, a public key and a private key, wherein
  - the public key and the private key are a matching pair,
  - the private key configured for accessing one or more details of the blockchain transaction and is associated with a blockchain-enabled medical implant, and
  - the private key is stored by a blockchain-enabled medical implant in the patient; and
- adding the blockchain transaction to a distributed ledger of transactions associated with the patient, wherein the blockchain transaction is added to a private ledger or as a private transaction to a public ledger.

* * * * *